(12) United States Patent
Hissink et al.

(10) Patent No.: US 8,481,651 B2
(45) Date of Patent: Jul. 9, 2013

(54) BIODEGRADABLE MULTI-BLOCK CO-POLYMERS

(75) Inventors: Catharina Everdina Hissink, Groningen (NL); Rob Steendam, Groningen (NL); Ronald Meyboom, Haren (NL); Theodorus Adrianus Cornelius Flipsen, Groningen (NL)

(73) Assignee: Innocore Technologies B.V., Groningen (NL)

( * ) Notice: Subject to any disclaimer, the term of this patent is extended or adjusted under 35 U.S.C. 154(b) by 978 days.

(21) Appl. No.: 10/586,226

(22) PCT Filed: Jan. 14, 2005

(86) PCT No.: PCT/NL2005/000020
§ 371 (c)(1),
(2), (4) Date: Dec. 14, 2006

(87) PCT Pub. No.: WO2005/068533
PCT Pub. Date: Jul. 28, 2005

(65) Prior Publication Data
US 2007/0155906 A1    Jul. 5, 2007

(30) Foreign Application Priority Data

Jan. 15, 2004    (EP) ..................................... 04075099

(51) Int. Cl.
*C08G 63/91*    (2006.01)

(52) U.S. Cl.
USPC ......................................................... 525/415

(58) Field of Classification Search
USPC ................. 525/415, 450, 454, 460, 410, 411, 525/413, 418, 419, 437, 449, 461
See application file for complete search history.

(56) References Cited

U.S. PATENT DOCUMENTS

| | | | |
|---|---|---|---|
| 4,806,658 A * | 2/1989 | Chang et al. ................... | 549/368 |
| 5,665,831 A | 9/1997 | Neuenschwander et al. | |
| 5,916,998 A | 6/1999 | Ferruti et al. | |
| 6,160,084 A * | 12/2000 | Langer et al. ................. | 528/272 |
| 6,413,539 B1 * | 7/2002 | Shalaby ......................... | 424/426 |
| 7,425,322 B2 * | 9/2008 | Cohn et al. ................. | 424/78.02 |
| 2003/0139567 A1 | 7/2003 | Kim et al. | |
| 2006/0178477 A1 | 8/2006 | Neuenschwander | |

FOREIGN PATENT DOCUMENTS

| | | |
|---|---|---|
| JP | 08-059811 | 3/1996 |
| JP | 10-046013 | 2/1998 |
| JP | 11-35655 | 2/1999 |
| JP | 2002-371259 | 12/2002 |
| JP | 2003-192774 | 7/2003 |
| JP | 2009-513747 | 4/2009 |
| WO | WO 98/02171 | * 11/1997 |
| WO | WO-98/02171 | 1/1998 |
| WO | WO-99/18142 | 4/1999 |
| WO | WO-99/29758 | 6/1999 |
| WO | WO 03/080119 | * 10/2003 |

OTHER PUBLICATIONS

Rashkov, I.; Manolova, N.; Li, S.M.; Espartero, J.L.; Vert, M.; Macromolecules, 1996, p. 50-56.*
Gorna, K.; Gogolewski, S.; Biodegradable Polyurethanes for Implants, 2001, p. 592-606.*
Sheet 1, Fox Equation [online], accessed via the Internet [retrieved on Apr. 16, 2010], URL: <http://www.polymerchemistryhypertext.com/FoxEquation.htm>.*
Sheet 2, Alfa Aesar lactide pricing information [online], accessed via the Internet [retrieved on Apr. 16, 2010], URL: <http://www.alfa.com/en/gp140w.pgm>.*
International Search Report for PCT/NL2005/000020, mailed on Apr. 21, 2005, 2 pages.

* cited by examiner

*Primary Examiner* — Robert Jones, Jr.
(74) *Attorney, Agent, or Firm* — Morrison & Foerster LLP

(57) ABSTRACT

The invention relates to a biodegradable multi-block copolymer, comprising at least two hydrolysable segments derived from pre-polymers A and B, which segments are linked by a multi-functional chain-extender and are chosen from the pre-polymers A and B, and triblock copolymers ABA and BAB, wherein the multi-block copolymer is amorphous at physiological (body) conditions. The invention further relates to a process for preparing said copolymer and to its use as a medical implant, a coating for a medical device or a drug delivery vehicle.

24 Claims, 5 Drawing Sheets

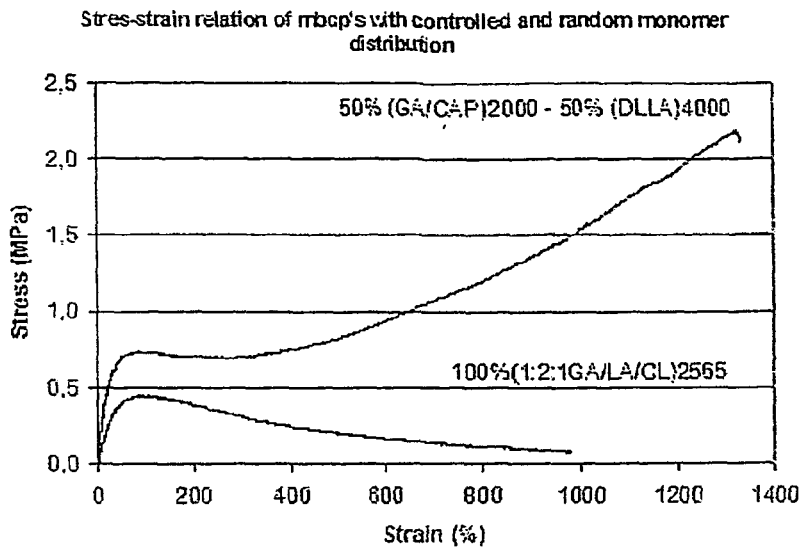

Figure 1a. Stress-strain curves of $100(GA_{50}LA_{25}CL_{25})_{2565}$ (entry 8, Table 2) with random monomer distribution and $50(GA_{50}CL_{50})_{2000}$-$50(LA)_{4000}$ (entry 2, Table 2) with controlled monomer distribution. For exact monomer composition, see Table 2

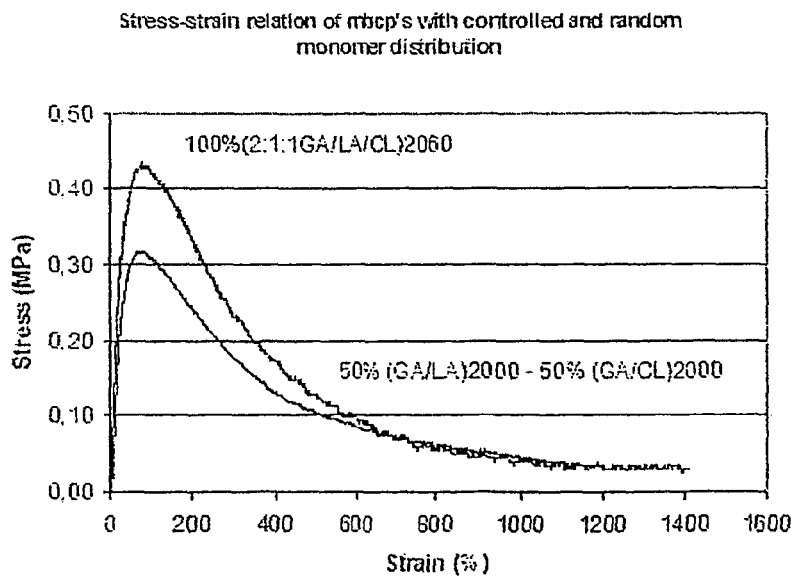

Figure 1b. Stress-strain curves of $100(GA_{50}LA_{25}CL_{25})_{2060}$ (entry 7, Table 2) with random monomer distribution and $50(GA_{50}LA_{50})_{2000}$ – $50(GA_{50}CL_{50})_{2000}$ (entry 5, Table 2) with controlled monomer distribution. For exact monomer composition, see Table 2.

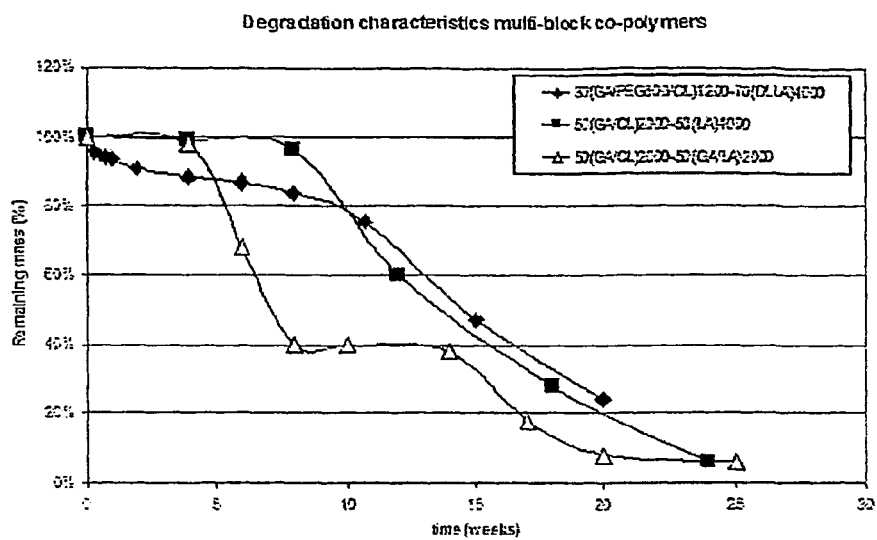
Figure 2: Mass loss characteristics of $30(GA_{50}CL_{50}\ PEG600)_{1200}$-$70(LA)_{4000}$ (entry 9, Table 2), $50(GA_{50}CL_{50})_{2000}$-$50(LA)_{4000}$ (entry 2, Table 2) and $50(GA_{50}CL_{50})_{2000}$-$50(GA_{50}LA_{50})_{2000}$ (entry 5, Table 2) urethane-linked multi-block co-polymers.

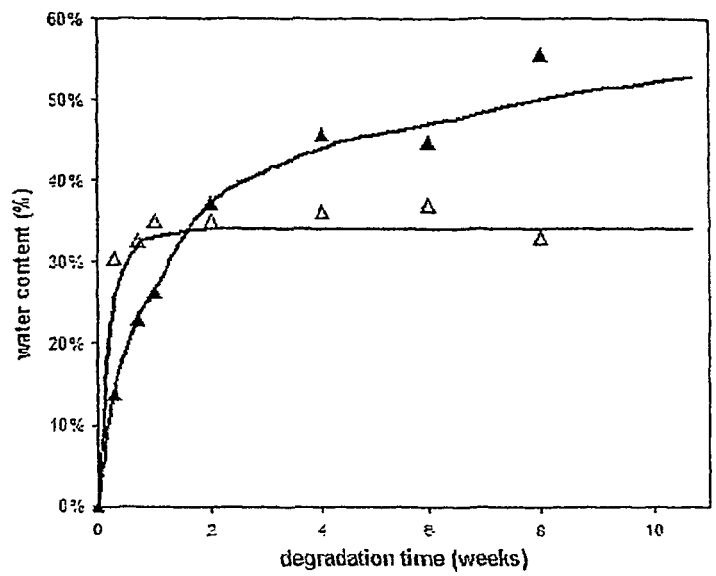

Figure 3a: Water uptake characteristics of $(GA_{50}CL_{50}\ PEG600)_{1200}$-$(LA)_{4000}$ urethane-linked multi-block co-polyesters with total PEG content of 15% (solid symbols; entry 9, Table 2) and 25% (open symbols; entry 10, Table 2).

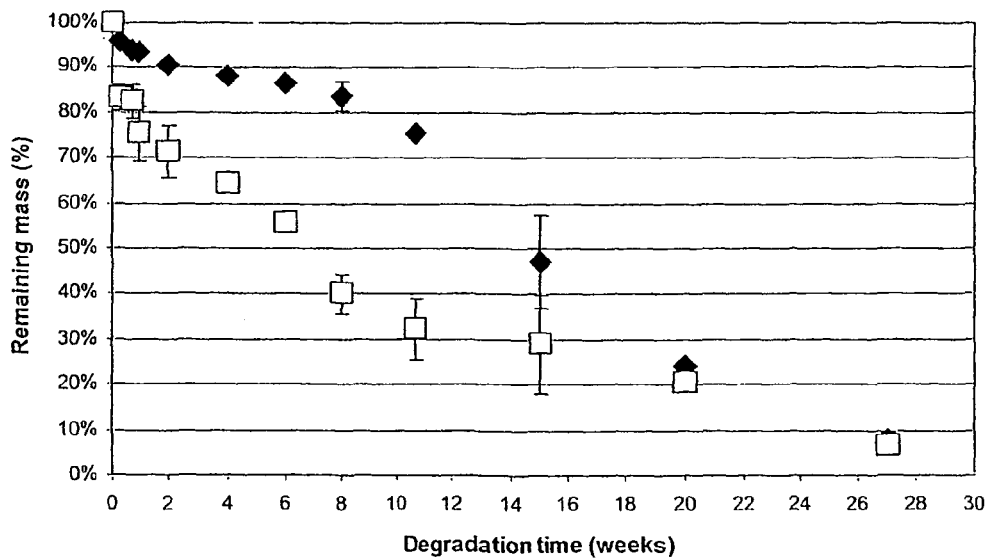

Figure 3b: Mass loss characteristics of $(GA_{50}CL_{50}\ PEG600)_{1200}$-$(LA)_{4000}$ urethane-linked multi-block co-polyesters with total PEG content of 15% (solid symbols; entry 9, Table 2)) and 25% (open symbols; entry 10, Table 2).

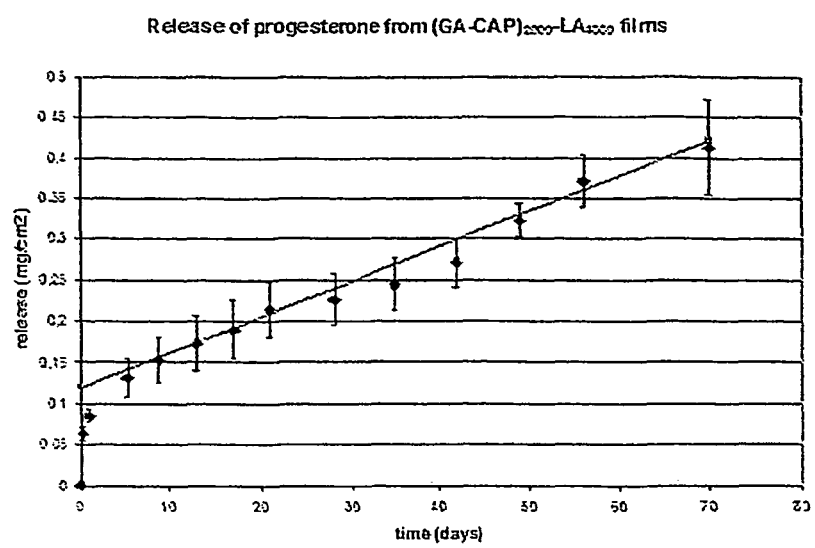
Figure 4 Cumulative release of progesterone from $50(GA_{50}CL_{50})_{2000}$-$50(LA_{4000})$ films

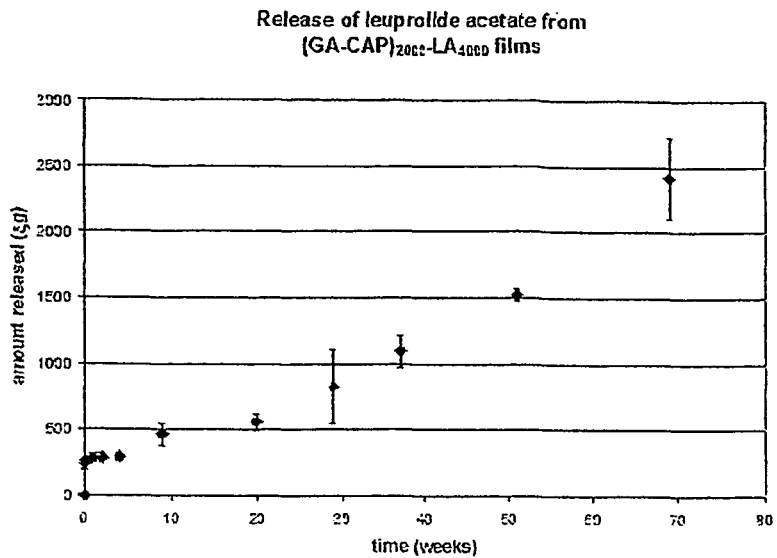

Figure 5. Cumulative release of leuprolide acetate from a urethane-linked $50(GA_{50}CL_{50})_{2000}$-$50(LA)_{4000}$ multi-block copolymer (drug load 20% w/w, film thickness 100 micron, sample weight 50-55 mg).

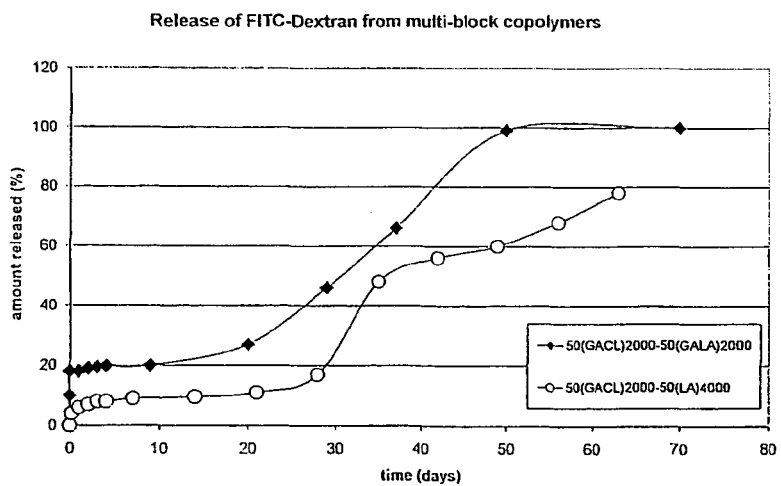

Figure 6 Effect of composition on cumulative release of FITC-dextran from urethane-linked $50(GA_{50}CL_{50})_{2000}$-$50(LA_{4000})$ and[ $50(GA_{50}CL)_{2000}$-$50(LA_{50}GA_{50})_{2000}$] multi-block copolyester films (drug load 12 and 20% w/w respectively, film thickness ~80 mm, sample weight 50-55 mg).

BIODEGRADABLE MULTI-BLOCK CO-POLYMERS

CROSS-REFERENCE TO RELATED APPLICATIONS

This application is a U.S. National Phase of PCT/NL2005/000020, filed on 14 Jan. 2005, which claims priority to European patent application 04075099.4, filed on 15 Jan. 2004. The contents of said applications are incorporated herein in their entirety.

The invention is directed to biodegradable, thermoplastic, multi-block copolymers. The copolymers of the present invention find use in various applications, particularly in the field of pharmaceutical drug delivery systems, drug-eluting coatings and biomedical implants.

The invention relates to biodegradable multi-block copolymers, the hydrolysable sequences being amorphous and the segments being linked by a multifunctional chain-extender, and the segments having different physical and degradation characteristics. For example, a multi-block co-polyester consisting of a glycolide-ε-caprolactone segment and a lactide-glycolide segment is composed of two different polyester pre-polymers. By controlling the segment monomer composition, segment ratio and length, a variety of polymers with properties that can easily be tuned can be obtained. These materials are particularly interesting for constructing drug delivery matrices, which contain and release a therapeutic agent, such as injectable drug-loaded biodegradable microspheres for controlled drug delivery, or drug-eluting coatings for medical devices.

Considerable research has been undertaken in the field of drug delivery matrices that contain and deliver various biologically active agents.

One reason for these research efforts is to develop pharmaceutical delivery systems, which prolong the release time of existing drugs. Many new drugs have short half-lives, which necessitates frequent injection schedules. Another reason is that many new drugs that may have been developed have poor pharmacokinetic profiles. In particular, peptides and proteins cause pharmacokinetic difficulties. Such substances must be administered parenterally if systemic action is required. Patient compliance and the high costs associated with frequent dosing protocols for parenterally administered drugs provide strong stimuli for the development of alternative dosage forms and dosing regimens.

Delivery matrices provided in the form of a coating, e.g. on a medical device, are often referred to as drug-eluting coatings. The major driver for the use of drug-eluting coatings is to improve the performance of the medical device, i.e. more successfully treating the disease and/or preventing or reducing undesired side reactions, such as inflammation or infection. Drug-eluting coatings allow the controlled release of biologically or pharmacologically active compounds due to which a therapeutically effective drug concentration can be achieved over a certain period of time. Drug-eluting coatings further allow local site-specific drug delivery. The drug can be delivered locally thereby allowing the achievement of high concentrations of the active compound at the site where it is most needed. Total drug doses may be significantly lowered thereby preventing the high systemic concentrations associated with oral administration of the frequently highly toxic drugs.

Polymeric systems which are presently under investigation as biodegradable drug delivery matrices for injectable or implantable pharmaceutical formulations and as drug-eluting coatings to be applied on medical devices include poly-D,L-Lactide (PDLLA), copolymers of lactide and glycolide (PLGA) (Brannon-Peppas, Int. J. Pharmaceutics, 116 (1995) p1-9; Couvreur, et al., Advanced Drug Delivery Reviews, 10 (1993) p141-162; Conti, et al., J. Microencapsulation, 9 (1992) p153-166 and copolymers of lactide and ε-caprolactone (Buntner et al, J. Control. Rel. 56 (1998) 159). PGLA is by far the most widely applied matrix system for injectable drug delivery systems. In the field of biodegradable materials for drug-eluting coatings, Drachman et al. (J. of American College of Cardiology, vol. 36, no. 7, 2000) reported on the use of poly(lactide-ε-caprolactone) (PLA-ε-CL) copolyesters as biodegradable coating material for the controlled release of paclitaxel from vascular stents. A fully degradable heparin-eluting (PLA-ε-CL) stent has been reported by Gao R. et al. (J. of American College of Cardiology, vol. 27, no. 85A, 1996 (abstract)). Polylactide (DL-PLA) and a polylactide-trimethylenecarbonate copolymer (PLA-co-TMC) have been used for the controlled release of dexamethasone from Strecker stents (Strecker E. P., et al., Effect on intimal hyperplasia of dexamethasone released from coated metal stents compared with non-coated stents in canine femoral arteries, Cardiovasc. Intervent. Radiol., 21 1998 p. 487. EP1254674 describes a polylactide acid (Mw=30 kDa) based stent coating for the controlled local delivery of tacrolimos. Bertrand O. F. et al., (Biocompatibility aspects of new stent technology, J. of American College of Cardiology, vol. 32, no. 3, 1998) reviewed several materials for use as matrix material for a drug-eluting coating. Van der Giessen et al. (Marked inflammatory sequalae to implantation of biodegradable and non-biodegradable polymers in porcine coronary arteries. Circulation 94 (1996) 1690) evaluated several materials, including PGLA and PCL for application as a drug-eluting coating on stents. Prietzel et al (Inhibition of neointimal proliferation with a novel hirudin/prostacyclin analog eluting stent coating in an animal overstretch model. Circulation 94 (1996) I-260) and Lincoff et al. (sustained local delivery of dexamethasone by a novel intravascular eluting stent to prevent restinosis in the porcine coronary injury model. J. Am. Coll. Cardiol. 29 (1997) 808-816) tested PLLA as a matrix for controlled delivery of their active compounds.

Amorphous PLGA copolymers and PDLLA homopolymers have a number of disadvantages when used in controlled drug-release applications. Due to their high sub-body temperature Tg's, both PLGA and PDLLA are rigid matrices. The ability to manipulate the release of an encapsulated drug, especially if the drug has a high molecular weight such as proteins, is therefore limited because of a limited diffusion of these molecules within PLGA and PDLLA matrices. The release of drugs from PLGA and PDLLA matrices, therefore, is initially solely governed by diffusion of dissolved drug molecules through pores. Only in a later stage, when hydrolytic degradation has lowered the molecular weight sufficiently or when (parts of) the polymer matrix start to dissolve, diffusion of drug molecules through the polymer matrix becomes possible, generally leading to dose dumping of the encapsulated drug. Furthermore, during degradation of PLGA and PDLLA, acidic degradation products (lactic and glycolic acid) are accumulating in the polymeric matrix due to its glassy character (Tg>37° C.), which may have a negative effect on sensitive actives such as proteins and peptides, but may be harmless to other drugs. Random copolymers of lactide and caprolactone (PLA-ε-CL) yield less acidic degradation products. Moreover, these copolymers are not associated with significant pH reductions in the polymer matrix if the polymer matrix is rubbery under body conditions, i.e. the Tg (glass transition temperature) of the copolymer is below appr.37° C. Under these conditions, the polymer matrix is also permeable to high molecular weight drugs and to the degradation products that are released, thereby preventing accumulation and as a result preventing the generation of an acidic environment. However, these materials are very sticky due to which processing into free flowing microspheres, which is a typical prerequisite for the formulation of injectable particulate drug delivery systems, is rather challenging. For the same reason, they are also difficult to handle when used as drug-eluting coatings on medical devices. Sticking can be greatly reduced by increasing the lactide content, but then the polymer will become too rigid. Increasing the caprolactone content can also reduce sticking, but then the overall degradation rate of the polymers becomes so low that accumulation of the polymer material at the site of the injection might occur upon repeated injections.

Furthermore, the physicochemical properties of the above mentioned (co)polymers can only be affected by three parameters: molecular weight, monomer ratio and monomer distribution, which is an important drawback if optimization of characteristics of pharmaceutical or medical formulations is required. Because the reactivity of glycolide, lactide and caprolactone towards ring-opening is very different and the high temperatures that are usually required for complete monomer conversion, it is difficult to obtain a controlled monomer distribution in this type of copolymers. Therefore, also randomly polymerized terpolymers, which are built of these monomers are not suitable enough to create a matrix of polymers with a wide range of polymer properties. Thus, there is an obvious need for the provision of new materials for drug delivery applications that overcome the above mentioned disadvantages of the currently used materials and provide better tools to control and optimize the characteristics of pharmaceutical or medical formulations, especially with respect to the release characteristics of encapsulated drugs.

This can be achieved by the use of biodegradable multi-block copolymers of the present invention, comprising segments of pre-polymers of different chemical composition and physico-chemical characteristics. By combining different segments with different physico-chemical properties, different functionalities can be built into the material, e.g. high swelling degree, increased permeability, or slow degradation rate. Moreover, weak and disadvantageous properties of one of the segments may be masked, whereas advantageous properties of the individual segments may be combined. Moreover, a functionality may be introduced without directly affecting other functionalities of the polymer. Moreover, by combining two segments of different composition, leading to a certain extent of phase separation, biphasic release patterns can be achieved. For example, if one of the segments has low permeability and/or is slowly degrading and the other segment has high permeability and/or degrades rapidly, encapsulated drug molecules will initially be released predominantly from the phase which has a high permeability and/or degrades rapidly, before release of drug molecules encapsulated in the phase with lower permeability/degradation rate will start to contribute significantly. By modifying the permeability and/or degradation rates of the two phases, the time at which release from a specific phase starts can be controlled.

Copolymers used as pharmaceutical drug delivery matrices, such as injectable microspheres or drug-eluting coatings, do not necessarily need to be rigid under body conditions. It is even considered an advantage that a drug-eluting implant, coating or microsphere is soft as this prevents tissue irritation due to mechanical friction. It is however beneficial that the materials are rigid under processing conditions as to prevent sticking. The latter is especially relevant when a therapeutical agent is encapsulated in microspheres if one wants to collect them as individual particles, and re-suspension of the (freeze-)dried formulation prior to injection may be problematic due to agglomerate formation. More important, injection into the body will be problematic, as the needle may be blocked easily due to agglomeration of the microspheres.

Besides the previously mentioned amorphous homo-and copolymers, also many block co-polyesters (AB, ABA and multi-block) have been studied in the past and are still under investigation for their drug loading and release properties. ABA type block copolymers that comprise a hydrophilic, non-biodegradable block such as polyethylene glycol (PEG) and a hydrolysable polyester block intended for drug release purposes are described in patent application U.S. Pat. No. 5,548,035. These copolymers are built of a polyethylene glycol central block and hydrophobic hydrolysable non-swellable outer hard block consisting of PLA, PGA, PLGA or PCL. Also block copolymers based on amorphous ester blocks (A) and hydrophilic ether groups B have been prepared. The amorphous character of the group A improves the solubility in organic solvents compared to ABA blocks based on crystallisable PGA or PLA sequences. ABA block (PELA) copolymers comprising poly(D,L-Lactide) (A) and PEG (B) blocks have also been studied for drug and protein loading efficiency: (Deng X M, Li X H, Yuan M L et al., J. Control. Release 1999, 58 123-31: Optimization of preparative conditions for poly DL-Lactide-polyethylene glycol microspheres with entrapped *Vibrio cholera* antigens" Deng X M, Zhou S B, Li X H, Zhao J, Yuan M L. In vitro degradation and release profiles for poly DL-Lactide-polyethylene glycol microspheres containing human serum albumin. J. Control. Release 2001, 71, 165-73. Other examples are disclosed in patent number U.S. Pat. No. 6,258,121, which describes the use of a blend of a hydrophilic lactide-polyethylene oxide copolymer (PLA-PEO) and a hydrophobic PLA-ϵ-CL copolymer as a stent coating for the controlled local delivery of paclitaxel into the blood vessel wall. Although polymer properties can be greatly improved by using block copolymers with blocks of different copolymers instead of homo- or random copolymers, they still have some disadvantages.

To obtain a minimum molecular weight of a block copolymer with e.g. an ABA structure, the sequences A and B must have a certain length. The blocks may independently behave as the individual homopolymers with similar composition. Properties of the ABA type block co-polymers can mainly be tuned by varying the composition of A and B blocks or, alternatively, by varying the A/B ratio or the length of blocks A and B. The properties of multi-block co-polymers wherein the blocks or segments are much shorter and linked together by a chemical reaction can also be affected by varying segment length and ratio. Properties such as stiffness, permeability, swelling characteristics and degradation behaviour and also drug release characteristics can be tuned in a much better way. Examples of known multi-block co-polymers are those described by Penco et al. (M. Penco, S. Marcioni, P. Ferruti, S. D'antone and R. Deghenghi, Biomaterials 17 (1996) 1583-1590) concerning multi-block co-polymers containing poly (lactide/glycolide) and polyethylene glycol segments and by Li et al. (S. Li, H. Gareau. M. Vert, T. Petrova, N. Manolova, I. Rashkov, J. of Appl. Pol. Science 68, (1998) 989-998 who describes multi-block co-polymers of poly(ϵ-caprolactone) and polyethylene glycol segments. However, both type of multi-block co-polymers contain only one hydrolysable polyester segment, the other segment being non-hydrolysable (PEG). The freedom to vary with degradation and physical properties is therefore mainly restricted to the composition of the hydrolysable segment.

Penco et al. (European Polymer Journal, 36 (5), 2000, 901-908) also studied and described the preparation of amorphous multi-block co-polymers with structure (PGLA50/50-PCL530)n comprising two different hydrolysable amorphous segments. However, by using their preparation method, comprising phosgene, only multi-block co-polymers with alternating PCL530 en PGLA50/50 segments can be obtained. This method is therefore restricted to the preparation of multi-block co-polyesters with equimolar amounts of the two individual segments, thus limiting the possibilities to vary the composition and monomer distribution of multi-block copolymers.

The multi-block copolymers of the present invention comprise at least two pre-polymer segments with different chemical composition and both segments containing hydrolysable groups, such as ester, carbonate and/or anhydride groups and the pre-polymers having significantly different physicochemical properties. Furthermore, the multi-block copolymers of this invention are preferably substantially completely amorphous under body conditions. More in particular, a copolymer according to the invention is a biodegradable multi-block copolymer, comprising two hydrolysable segments, with different chemical composition, derived from two different pre-polymers A and B, wherein the pre-polymers A and B or triblock (pre-)copolymers with structure ABA and BAB are linked by a multi-functional chain-extender, and wherein the copolymer is amorphous under physiological (body) conditions. The multi-functional chain-extender is preferably an aliphatic chain-extender.

BRIEF DESCRIPTION OF THE DRAWINGS

FIG. 1a shows stress-strain curves of $100(GA_{50}LA_{25}CL_{25})_{2565}$ (entry 8, Table 2) with random monomer distribution and $50(GA_{50}CL_{50})_{2000}\text{-}50(LA)_{4000}$ (entry 2, Table 2) with controlled monomer distribution. For exact monomer composition, see Table 2.

FIG. 1b shows stress strain curves of $100(GA_{50}LA_{25}CL_{25})_{2060}$ (entry 7, Table 2) with random monomer distribution and $50(GA_{50}LA_{50})_{2000}\text{-}50(GA_{50}CL_{50})_{2000}$ (entry 5, Table 2) with controlled monomer distribution. For exact monomer composition, see Table 2.

FIG. 2 shows mass loss characteristics of $30(GA_{50}CL_{50}PEG600)_{1200}\text{-}70(LA)_{4000}$ (entry 9, Table 2), $50(GA_{50}CL_{50})_{2000}\text{-}50(LA)_{4000}$ (entry 2, Table 2) and $50(GA_{50}CL_{50})_{2000}\text{-}50(GA_{50}LA_{50})_{2000}$ (entry 5, Table 2) urethane-linked multi-block co-polymers.

FIG. 3a shows water uptake characteristics of $(GA_{50}CL_{50}PEG600)_{1200}\text{-}(LA)_{4000}$ urethane-linked multi-block co-polyesters with total PEG content of 15% (solid symbols; entry 9, Table 2) and 25% (open symbols; entry 10, Table 2).

FIG. 3b shows mass loss characteristics of $(GA_{50}CL_{50}PEG600)_{1200}\text{-}(LA)_{4000}$ urethane-linked multi-block co-polyesters with total PEG content of 15% (solid symbols; entry 9, Table 2) and 25% (open symbols; entry 10, Table 2).

FIG. 4 shows cumulative release of progesterone from $50(GA_{50}CL_{50})_{2000}\text{-}50(LA)_{4000}$ films.

FIG. 5 shows cumulative release of leuprolide acetate from a urethane-linked $50(GA_{50}CL_{50})_{2000}\text{-}50(LA)_{4000}$ multi-block co-polymer (drug load 20% w/w, film thickness 100 micron, sample weight 50-55 mg.).

FIG. 6 shows effect of composition on cumulative release of FITC-dextran from urethane-linked $50(GA_{50}CL_{50})_{2000}\text{-}50(LA_{4000})$ and $[50(GA_{50}CL)_{2000}\text{-}50(LA_{50}GA_{50})_{2000}]$ multi-block co-polyester films (drug load 12 and 20% w/w respectively, film thickness ~80 mm, sample weight 50-55 mg).

DETAILED DESCRIPTION OF THE INVENTION

In accordance with the invention, the term "pre-polymer" refers to the chemical units or building blocks making up the multi-block copolymer of the present invention. The pre-polymers usually have the notation A and B. It is to be noted that in the context of the invention, the term pre-polymer may also refer to a block copolymer of short length, e.g. of the structure ABA or BAB, but also to the building blocks A and B, if they are themselves polymers, of which these structures are composed. Each pre-polymer may be obtained by polymerization of suitable monomers, which monomers thus are the building blocks of each pre-polymer. The desired properties of the pre-polymers and, by consequence, of the copolymer of the present invention may be controlled by choosing a pre-polymer of a suitable composition and molecular weight (in particular number average molecular weight (Mn)), such that the desired Tg is obtained.

The term "multi-block" copolymer refers to copolymers with alternating or randomly distributed segments of short length, the segments being connected to each other by a chain-extender, and are also called "segmented" copolymers. The multi-block copolymers include chain-extended ABA and BAB block co-polymers.

"Tg" refers to the glass transition temperature of the polymer. The Tg may be measured by DSC (differential scanning calorimetry), DMTA (dynamic mechanical thermal analysis) or by other techniques suitable to measure reversible thermal transitions. The glass transition temperature, Tg, is determined by taking the midpoint of the specific heat jump, as may be measured e.g. by differential scanning calorimetry (DSC). A more detailed description of how the Tg is measured in accordance with the invention can be found in the appended examples.

It is to be understood that the glass transition temperature, Tg, as used herein refers to the corresponding value of a material when measured in dry state. However, when "Tg at physiological (body) conditions" is used, this is the Tg of the polymer when applied in vivo; viz. when at equilibrium with an atmosphere that is saturated with water and at body temperature. This Tg may be simulated in vitro by performing the DSC measurement after allowing the material to equilibrate with a water-saturated atmosphere for 1 hour at a temperature that matches body temperature. When in dry state, the multi-block co-polymers used in the present invention may have Tg values that are somewhat higher than at mammalian body conditions, that is to say, when the dry materials are subjected to DSC, the first inflection point may arise at higher temperatures, for instance at 42 or 50° C., or more. Upon application in vivo, however, the dry material's Tg will drop as a result of the absorption of water. This final Tg is defined as the "Tg at physiological (body) conditions".

Human body conditions are normal conditions for a healthy person, for example a body temperature of appr. 37° C. and a moist environment. The polymers of this invention may also be applied in mammals other than human, but then the body conditions may be different, for instance the body temperature may be lower or higher than 37° C., depending on the type of mammal.

The polymers of this invention are completely amorphous at physiological (body) conditions. However, in the dry state, the polymer may be partly crystalline, which crystallinity disappears shortly after submission to a physiological environment, i.e. appr. 37° C. in moist environment for humans. For instance, a polymer that contains PEG in one of the segments can be crystalline under dry conditions at ambient temperature, while amorphous under wet conditions, giving either a mixed Tg or two separated Tg's of this segment as a result of the amorphous softened PEG and the polyester/carbonate. The amorphous multi-block co-polymers of the present invention may either be phase-mixed (one Tg) or phase-separated (two or more Tg's) even without the presence of PEG. Whereas a single pre-polymer is usually characterized by a single phase-transition (Tg), phase-separated multi-block copolymers are characterized by at least two phase-transitions, each of which is related to (but not necessarily identical to) the corresponding Tg values of the pre-polymers, which are comprised in the copolymer. In case of complete molecular immiscibility of the pre-polymers, the resulting Tg's of the multi-block co-polymer are governed solely by the contribution of the individual Tg' of the amorphous pre-polymers comprised in the copolymer. In most cases, however, partially or complete phase mixing of the pre-polymer based segments occurs. In case of complete phase mixing only one value of Tg is observed; in case of a partially phase mixed copolymer, at least two values of Tg are present, which generally lie between those of the individual pre-polymer segments when they would be present in a copolymer based entirely on one of these pre-polymers. The value of the Tg (or more) of the copolymer is further affected by the type and content of the chain-extender. The extent of miscibility of the segments is dependent on the pre-polymer composition, ratio and segment length in the copolymer, but the type of chain-extender may also affect it. The multi-block co-polymer may contain a crystalline phase: (e.g. when polyethylene glycol, PEG, is part of the pre-polymer) in the 'dry' state, which becomes amorphous in the 'wet' state. A wide range of amorphous multi-block copolymers can be obtained, with properties that lie between those of the rigid homo-and copolymers and those of the rubbery copolymers of the prior art. Depending on the type of application, the pre-polymers and chain-extender may be chosen in such a way to obtain a polymer or a polymer-drug formulation with the desired properties.

A multi-block copolymer according to the invention is composed of pre-selected blocks having specific properties, e.g. thermal, physicochemical, and degradation properties. Suitable combinations of pre-polymers in the copolymer lead to specific properties of the copolymer, other than in case of random copolymers. The final segmented copolymer may possess specific properties of the individual pre-polymers, as well as additional properties obtained by the combination of the segments.

Another disadvantage of ABA type block copolymers over the multi-block copolymers is that they must be prepared at relatively high temperatures (>100° C.) under inert conditions for complete conversion of all the monomers and to obtain sufficient molecular weight. Furthermore, by the process of preparing ABA block copolymers (and derivatives thereof), there is always a possibility of trans-esterification, resulting in a less well-controlled monomer sequence.

The multi-block copolymers of the present invention do not suffer from this disadvantage since they can be prepared by linking pre-polymers with previously determined monomer composition at rather low temperatures (<100° C.). This will avoid trans-esterification and other side-reactions, which may cause the generation of undesired degradation and other by-products. This also means that the monomer sequence length of the copolymer is determined by the choice of building components and not so much by reaction time and temperature, as will be the case for synthesis of random- and block copolymers. An advantage of multi-block copolymers of this invention over the known alternating multi-block copolymers is that they can be prepared by linking of pre-polymers using a multifunctional chain-extender, thus obtaining a copolymer with pre-polymer segments randomly distributed in the copolymer. In accordance with the invention, multi-block copolymers wherein the pre-polymer segments are randomly distributed in the copolymer are preferred. All possible pre-polymer ratios and segment lengths can be used, thus offering a wider range of possibilities to tune the properties.

By the same chain-extension method, perfectly alternating multi-block copolymers ((ABA)n or (BAB)n) can be obtained. An advantage of these multi-block co-polymers over the tri-block copolymers ABA and BAB of the prior art is that the molecular weight increases by chain-extending the relatively short tri-block pre-polymers and not by monomer conversion. Although the pre-polymers are also prepared at relatively high temperatures (>100° C.), complete monomer conversion is reached within a shorter reaction time, thus resulting in less trans-esterification and a more controlled monomer distribution. During chain-extension, the reaction conditions do not affect the monomer distribution in the multi-bock co-polymer.

The multi-block co-polymers of the present invention are composed of two different hydrolysable pre-polymers, either one or both may contain a hydrophilic segment (such as PEG initiator). The properties of the copolymer can be tuned by varying the composition of both segments, including the type of initiator (which may be hydrophilic or not), the ratio and the length of the segments. The method of preparing such copolymers by linking the pre-polymers with a multifunctional chain-extender offers the opportunity to influence the polymer properties by the type and amount of chain-extender. Since the initiator and chain-extender may both act as a softener, they can be chosen in such a way that a polymer with the desired Tg is obtained. Thus, instead of using certain monomers to lower the Tg (e.g. caprolactone) the chain-extender and initiator can be used for this purpose. By this method, soft and flexible non-sticky polymers may be obtained. The total degree of freedom to obtain polymers with the desired properties is therefore increased as compared to polymers of the prior art. This is an important aspect as it allows easy adjustment of the polymer characteristics to optimize the release characteristics of a specific drug.

Parameters, which may be used to modify the physicochemical properties, and consequently the release characteristics, include type and amount of monomers in the segments, type of initiator, molecular weight of the segments, weight percentage of different segments, overall molecular weight of the multi-block copolymer and type and content of chain-extender.

The amorphous character of the multi-block copolymers makes these polymers especially suitable for drug delivery and medical coating purposes. Usually, tightly controlled permeability and degradation characteristics (rate) are required to control the release rate, period of release and to achieve that the empty polymer matrix is resorbed from the site of injection shortly after completion of the release. A phase transition of the polymer below body temperature and at physiological (body) conditions makes the materials very suitable as an implant in the body as they soften under physiological conditions and give a favorable interaction with the surrounding tissue and lower the chance on tissue irritation as compared to rigid implants. Sometimes a more rigid material is preferred, for example when the release rate of a drug is too fast from a rubbery matrix. Then the disadvantages of the rigid polymers are less important and are acceptable for the type of application.

The materials of the present invention have thermal properties that allow processing of the material in the melt at relatively low temperatures, thus avoiding trans-esterification and other side-reactions that cause the generation of undesired degradation and other by-products. At the same time, the thermal properties are such that the materials can be used as a biomedical implant.

General Polymer Structure

The multi-block copolymers of this invention preferably comprise two hydrolysable segments having a different composition, linked by a multifunctional, preferably an aliphatic chain-extender, and which are preferably essentially completely amorphous under physiological conditions. (moist environment, body temperature, which is appr 37° C. for humans).

The resulting multi-block copolymers of the present invention preferably have a structure according to any of the formulae (1)-(3):

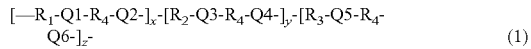  (1)

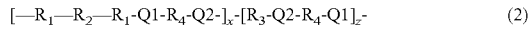  (2)

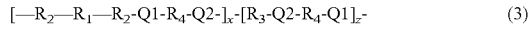  (3)

wherein $R_1$ and $R_2$ may be amorphous polyester, amorphous poly ether ester or amorphous polycarbonate; or an amorphous pre-polymer that is obtained from combined ester, ether and/or carbonate groups. $R_1$ and $R_2$ may contain polyether groups, which may result from the use of these compounds as a polymerization initiator, the polyether being amorphous or crystalline at room temperature. However, the polyether thus introduced will become amorphous at physiological conditions. $R_1$ and $R_2$ are derived from amorphous pre-polymers or blocks A and B, respectively, and $R_1$ and $R_2$ are not the same. $R_1$ and $R_2$ may contain a polyether group at the same time, but it is preferred that only one of them contains a polyether group;

z is zero or a positive integer;

$R_3$ is a polyether, such as poly(ethylene glycol), and may be present (z≠0) or not (z=0). $R_3$ will become amorphous under physiological conditions;

$R_4$ is an aliphatic $C_2$-$C_8$ alkylene group, optionally substituted by a $C_1$-$C_{10}$ alkylene, the aliphatic group being linear or cyclic, wherein $R_4$ is preferably a butylene, —$(CH_2)_4$— group, and the $C_1$-$C_{10}$ alkylene side group may contain protected S, N, P or O moieties;

x and y are both positive integers, which are both preferably at least 1, whereas the sum of x and y (x+y) is preferably at most 1000, more preferably at most 500, most preferably at most 100. Q1-Q6 are linking units obtained by the reaction of the pre-polymers with the multifunctional chain-extender. Q1-Q6 are independently amine, urethane, amide, carbonate, ester or anhydride. The event that all linking groups Q are different being rare and not preferred.

Typically, one type of chain-extender may be used with three pre-polymers having the same end-groups, resulting in a copolymer of formula (1) with six similar linking groups. In case pre-polymers $R_1$ and $R_2$ are differently terminated, two types of groups Q will be present: e.g. Q1 and Q2 will be the same between two linked pre-polymer segments $R_1$, but Q1 and Q2 are different when $R_1$ and $R_2$ are linked. Obviously, when Q1 and Q2 are the same, it means that they are the same type of group but as mirror images of each other.

In copolymers of formula (2) and (3) the groups Q1 and Q2 are the same when two pre-polymers are present that are both terminated with the same end-group (which is usually hydroxyl) but are different when the pre-polymers are differently terminated (e.g. PEG which is diol terminated and a di-acid terminated 'tri-block' pre-polymer). In case of the tri-block pre-polymers ($R_1R_2R_1$ and $R_2R_1R_2$), the outer segments should be essentially free of PEG, because the coupling reaction by ring opening can otherwise not be carried out successfully. Only the inner block can be initiated by a PEG molecule.

The examples of formula (1), (2) and (3) show the result of the reaction with a di-functional chain-extender and di-functional pre-polymers.

With reference to formula (1) the polyesters of the present invention may also be represented as multi-block or segmented copolymers having a structure (ab)n with alternating a and b segments or a structure (ab)r with a random distribution of segments a and b, wherein 'a' corresponds to the segment $R_1$ derived from pre-polymer (A) and 'b' corresponds to the segment $R_2$ derived from pre-polymer (B) (for z=0). In (ab)r, the a/b ratio (corresponding to x/y in formula (1)) may be unity or away from unity. The pre-polymers can be mixed in any desired amount and can be coupled by a multifunctional chain extender, viz. a compound having at least two functional groups by which it can be used to chemically link the pre-polymers. Preferably this is a di-functional chain-extender. In case z≠0, then the presentation of a random distribution of all the segments can be given by (abc)r were three different pre-polymers (one being e.g. a polyethylene glycol) are randomly distributed in all possible ratio's. The alternating distribution is given by (abc)n. In this particular case, alternating means that two equally terminated pre-polymers (either a and c or b and c) are alternated with a differently terminated pre-polymer b or a, respectively, in an equivalent amount (a+c=b or b+c=a). Those according to formula (2) or (3) have a structure (aba)n and (bab)n wherein the aba and bab 'triblock' pre-polymers are chain-extended with a di-functional molecule.

The method to obtain a copolymer with a random distribution of a and b (and optionally c) is far more advantageous than when the segments are alternating in the copolymer such as in (ab)n with the ratio of pre-polymers a and b being 1. The composition of the copolymer can then only be determined by adjusting the pre-polymer lengths. In general, the a and b segment lengths in (ab)n alternating copolymers are smaller than blocks in block-copolymers with structures ABA or AB.

The pre-polymers of which the a and b (and optionally c) segments are formed in (ab)r, (abc)r, (ab)n and (abc)n are linked by the di-functional chain-extender. This chain-extender is preferably a diisocyanate chain-extender, but can also be a diacid or diol compound. In case all pre-polymers contain hydroxyl end-groups, the linking units will be urethane groups. In case (one of) the pre-polymers are carboxylic acid terminated, the linking units are amide groups. Multi-block copolymers with structure (ab)r and (abc)r can also be prepared by reaction of di-carboxylic acid terminated pre-polymers with a diol chain extender or vice versa (diol terminated pre-polymer with diacid chain-extender) using a coupling agent such as DCC (dicyclohexyl carbodiimide) forming ester linkages. In (aba)n and (bab)n the aba and bab pre-polymers are also preferably linked by an aliphatic di-functional chain-extender, more preferably, a diisocyanate chain-extender.

The term "Randomly segmented" copolymers refers to copolymers that have a random distribution (i.e. not alternating) of the segments a and b: (ab)r or a, b and c: (abc)r.

Synthesis Methods:

Multi-block co-polymers with structure (ab)r and (abc)r can be made by chain-extending a mixture of the pre-polymers, containing the monomers that form segments $R_1$ and $R_2$ (and optionally $R_3$), in the desired ratio with an equivalent amount of a di-functional molecule, preferably an aliphatic molecule, more preferably a diisocyanate such as 1,4-butanediisocyanate (BDI).

The polymerisation reaction can be carried out either in the bulk or in solution. The reaction can be carried out in the bulk at a temperature at which the pre-polymer mixture is a melt and which is at least 20° C. higher than the phase transition temperature of the pre-polymer. Polymerization takes place at this temperature for a time long enough to obtain an intrinsic viscosity of the copolymer of about 1 dl/g. Solid state post polymerization at room temperature may increase the molecular weight to an intrinsic viscosity up to 4 dl/g. Polymerization in solution offers many advantages and is therefore the preferred method. The pre-polymer(s) are dissolved in an inert organic solvent and the chain-extender is added pure or diluted with solvent. A solution of the pre-polymers is more homogeneous than a pre-polymer mixture in the bulk and can be made at a much lower temperature (below the melting point of the pre-polymers). The chain-extender can be mixed very fast with the pre-polymer solution. The polymer concentration and reaction temperature can be varied in order to control the polymerization reaction (e.g. viscosity of a solution can easily be monitored) and polymer properties such as the molecular weight. The solvent must have a sufficiently high boiling point for the polymerization reaction to proceed, which is preferably more than 60° C., more preferably more than 70° C. The solvent must be able to solve the resulting polymer in at least 1% (w/w), preferably more than 5% (w/w), more preferably more than 10% (w/w). Suitable solvents are for instance 1,4-dioxane, DMSO, NMP or DMF or solvents with similar solubility properties, which are known in the art. The preferred solvent is 1,4-dioxane. The polymer solution can be precipitated into water or organic non-solvents. In case a (very) hydrophilic polymer is made (as is the case with some of the polymers of this invention), a precipitation step into water is undesirable. The polymer will swell and may be difficult to isolate and completely dry without some degradation taking place.

A great advantage of using 1,4-dioxane as a solvent is its possibility to be removed by freeze-drying. Furthermore, the polymer solutions in dioxane can be easily formed into solid materials such as polymeric films by evaporation of the solvent at rather low temperatures.

The specific polymerization time and temperatures for some bulk and solution polymerizations are given in the examples below, but may be different for other pre-polymer combinations.

These polymerization methods are also applicable to segmented co-polymers with structures (aba)n and (bab)n. The chain-extension reaction of pre-polymers will not give rise to any trans-esterification due to the low polymerization temperature and short polymerization time and a preferred reaction of hydroxyl end-groups with the diisocyanate group. This will prevent trans-esterification so that the segmented structure is obtained and the monomer distribution is the same as in the pre-polymers that build the copolymer.

The alternating multi block-copolymers (ab)n are preferably formed by reacting (end-capping) one of the pre-polymers with at least two equivalents of a di-functional chain-extender, removing the excess of chain-extender and than add the other pre-polymer in about 1:1 ratio. The chain-extension reaction to obtain the alternating multi-block co-polymer is preferably carried out in solution, but is also possible in bulk. In case of copolymers with structure (abc)n, two pre-polymers can simultaneously be end-capped in the desired ratio and subsequently chain-extended with an equivalent amount of the $3^{rd}$ pre-polymer, or vice versa: one pre-polymer can be end-capped and then chain extended with an equivalent amount of a mixture of two pre-polymers.

Coupling reactions with DCC are preferably carried out in solution. Two (or three) pre-polymers that are all diol or diacid terminated are mixed in solution with a diacid or diol terminated chain-extender, respectively, after which DCC is added.

The materials obtained by chain-extending in the bulk can also be produced in situ in an extruder.

Pre-polymers of which the multi-block copolymers with structures (aba)n or (bab)n can be prepared, are generally made by addition of the monomer(s) of which the outer block will be formed to a pre-polymer with monomers that form the inner block. These methods are known in the art. Since the ABA and BAB pre-polymers are built of relatively short segments, the pre-polymer can subsequently be chain-extended with a di-functional molecule by the method described above. If the chain-extender is a difunctional, aliphatic molecule and the pre-polymers are linear, a linear co-polymer is made; if one of the reactants (either the chain-extender or at least one of the pre-polymers) or both have more than two functional groups, cross-linked structures are obtained. Preferably, the chain-extender is an aliphatic di-isocyanate, more preferably 1,4-butanediisocyanate.

The combination of pre-polymers is preferably chosen in such a way that a multi-block co-polyester or polyester-carbonate with the desired physicochemical, mechanical, thermal and degradation properties is obtained. Although most of the multi-block copolymers are characterized by a single glass transition temperature (except for an additional crystalline polyether melting point that may be present at ambient, dry conditions) the polymers may have properties that are determined by the individual components, due to a certain extent of phase separation. In some cases more than one glass transition temperature may be observed as a result of this phase separation. Because the two phases are chemically linked, the polymer properties will be different from e.g. blends of two polymers containing similar monomers than the linked pre-polymers.

Preferred Pre-polymers:

The hydrolysable segments $R_1$ and $R_2$ of formula (1) are formed by reaction of pre-polymers A and B with a chain-extender.

Pre-polymers (A) and (B) may e.g. be prepared by ring-opening polymerization. A pre-polymer may be a hydrolysable co-polymer prepared by ring-opening polymerization initiated by a diol or di-acid compound, preferably having a random monomer distribution. The diol compound is preferably an aliphatic diol or a low molecular weight polyether. The polyether may be PEG (polyethylen eglycol), PEG-PPG copolymers (polypropylene glycol) or PTMG (poly tetramethylene glycol) and combinations thereof. The polyether is preferably PEG and can be part of the pre-polymer by using it as a diol initiator or it can be mixed with the pre-polymers, thus forming hydrophilic segment $R_3$ in formula (1).

The pre-polymers A and B may be a hydrolysable polyester, poly ether ester, polycarbonate, polyester carbonate, polyanhydride or copolymers thereof, derived from cyclic monomers such as lactide (L, D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). In order to obtain polymers with a glass transition temperature below appr. 37° C. at physiological (body) conditions, some of the above-mentioned monomers or combinations of monomers are more preferred than others.

Furthermore, the pre-polymers can be based on (mixtures of) condensation type of monomers such as hydroxyacids (e.g. lactic acid, glycolic acid, hydroxybutyric acid), diacids (e.g. glutaric, adipic or succinic acid, sebacic acid) and diols such as ethylene glycol, diethylene glycol, 1,4-butanediol or 1,6-hexanediol, forming ester and/or anhydride hydrolysable moieties.

Polymers of formula's (2) and (3) are composed of segments $R_1$ and $R_2$ with monomer compositions similar to those of formula (1), except that $R_1$ of formula (2) and $R_2$ of formula (3) can not comprise an initiator, since the inner segments ($R_2$ of formula (2) and $R_1$ of formula (3)) act as an initiator for the polymerization of the outer segments.

Pre-polymers containing aromatic groups are generally not suitable for obtaining amorphous multi-block co-polymers of the present invention, because these pre-polymers will have a phase transition temperature that is too high (>100° C.). Furthermore, the processing temperature is high, the solubility in common organic solvents is generally too low and pre-polymers containing aromatic groups may give rise to undesired degradation products. This also holds true for the chain-extenders that are used; it is generally not preferred to use chain-extenders containing aromatic groups, more specific aromatic groups with multi-functional isocyanate groups, because degradation of multi-block co-polymers containing aromatic moieties may lead to the formation of suspected carcinogenic compounds, such as aromatic diamines. This makes them less suitable for application in biodegradable medical devices. Furthermore, the transition temperature of multi-block copolymers containing aromatic groups may be too high for the intended applications. Therefore, aliphatic chain-extenders are preferred.

It will be understood that the pre-polymers A and B are composed of different monomers or contain the same monomers but in a different amount or that the pre-polymer is composed of the same monomers but with a different initiator in order to obtain the multi-block copolymers of the present invention, which means that the segments must have significantly different properties such as thermal, degradation and hydrophilic properties.

Typically, the pre-polymers or blocks A and B forming segment $R_1$ and $R_2$, respectively, have an Mn between 300 and 30.000, preferably larger than 500, more preferably larger than 1000 but less than 8000. The content of pre-polymer B in the multi-block copolymer is preferably 10-90 wt. %, more preferably 25-75 wt. %. Preferably, one of the pre-polymers (B) contains lactide. That particular pre-polymer may be a homopolymer of poly(DL-Lactide) or a copolymer of lactide/glycolide, preferably with a (50/50) ratio. The other pre-polymer or block (A) is preferably built of at least two different monomers, one of which being a monomer that lowers the Tg of the resulting multi-block co-polymer below that of a co-polymer based entirely on pre-polymer B. Therefore it contains preferably a lactone or a cyclic carbonate, more preferably ε-caprolactone. The amount of ε-caprolactone in A does preferably not exceed 50%, since crystallization of poly-caprolactone may occur. The other component of pre-polymer or block A is preferably lactide or glycolide, in order to obtain a fast degrading polymer. In case an even faster degradation is preferred and/or a polymer with a rather high Tg is desired, pre-polymer A consists preferably of lactide and glycolide, with the condition that pre-polymer B has another composition. In case a slower degradation is required, trimethylene carbonate can be built in. In order to obtain a more hydrophilic segment, para-dioxanone can be used as a comonomer. Also PEG may be used as an initiator for this purpose. When PEG is used as an initiator of segment A or when a high content of initiator and/or chain-extender is present in the polymer, pre-polymer A does not necessarily have to contain a lactone or cyclic carbonate to lower the Tg of the polymer. The PEG initiated pre-polymer may even contain only one type of monomer (e.g. caprolactone or lactide).

The D/L ratio of the lactide used in poly-dl-lactide segments may be away from unity but is preferably (50/50). An excess of one of the stereo-isomers will increase the Tg of the poly-lactide pre-polymer. A pre-polymer or block B based on only one of the isomeric lactides (either L- or D-Lactide) is not preferred since this will result in crystalline segments in the co-polymer.

The pre-polymers will preferably be linear and random (co)polyesters or polyester-carbonates with reactive end-groups. These end-groups may be hydroxyl or carboxyl. It is preferred to have a dihydroxy terminated co-polyester, but hydroxy-carboxyl or dicarboxyl terminated polyesters can also be used. In case the polyester has to be linear, it can be prepared with a di-functional component (diol) as a starter, but in case a three- or higher functional polyol is used, star shaped polyesters may be obtained. The diol can be an aliphatic diol or a low molecular weight polyether. The polyether is preferably present as an initiator with an Mn between 150-4000, preferably between 150-2000, more preferably between 300-1000.

The pre-polymer synthesis is preferably carried out in the presence of a catalyst. A suitable catalyst is $Sn(Oct)_2$, stannous octoate, with a monomer/initiator ratio of M/I=5000-30000. It is also possible to carry out the synthesis without a catalyst.

The conditions for preparing the polyesters are those known in the art.

The copolymers of the present invention are generally linear. However, it is also possible to prepare the copolymers in a branched or cross-linked form. These non-linear copolymers of the present invention may be obtained by using a tri-(or higher) functional chain extender, such as tri-isocyanate. Branched copolymers may show improved creep characteristics (reduced creep tendency). Cross-linked copolymers are generally not preferred, since these copolymers are not easy to process.

Very high molecular weights of the linear multi-block copolymers are not necessary to obtain good mechanical properties. With an intrinsic viscosity of the copolymer of about 0.8 dl/g the initial mechanical properties will be sufficient for the production of medical devices and drug delivery applications. High intrinsic viscosities are undesirable, because the polymer will be difficult to process. Typically, the intrinsic viscosity is larger than 0.1 dl/g and less than 6 dl/g. Preferably, the intrinsic viscosity lies between 0.2-4 dl/g, more preferably between 0.4-2 dl/g.

During handling, processing, storage or transport, it is sometimes preferred that the device or product has a phase transition temperature above ambient temperatures, which is about 25° C. The polymer becomes less sticky and after application in the body, such a device may loose its stiffness and may soften at physiological conditions.

The multi-block co-polymers can be formed into surgical articles using any known technique such as, for example, extrusion, molding, solvent casting, and freeze drying. The latter technique is used to form porous materials. Porosity can be tuned by addition of co-solvents, non-solvents and/or leachables. Copolymers can be processed (either solid or porous) as films, sheets, tubes, membranes, coatings, meshes, microspheres, stents, foams and other articles. Products can be either solid, hollow or (micro)porous. A wide range of surgical articles can be manufactured for applications in for example wound care, skin recovery, nerve regeneration, vascular prostheses, tissue engineering, coating of medical and surgical devices, dental and orthopedic repair. The copolymers can be used alone or can be blended and/or co-extruded with other absorbable or non-absorbable polymers.

Furthermore, they can be used in pharmaceutical applications, e.g. for drug delivery, e.g. in the form of microspheres, injectable gel formulations, coatings or membranes or devices The invention accordingly also relates to drug delivery matrices, which contain and release a bioactive or therapeutic agent. More particularly, the invention relates to pharmaceutical injectable or implantable formulations and drug-eluting medical device coatings, such as stent coatings, which include a pharmacologically active agent encapsulated in a matrix comprising urethane linked multi-block copolymers, the blocks of which have different physical and degradation characteristics, such as, for example, a multi-bock co-polyester consisting of a poly(glycolide-caprolactone) segment $R_1$ and a poly(lactide-glycolide) segment $R_2$, the pre-polymer segments being chain-extended with 1,4-butanediisocyanate to form the urethane linkages.

The invention also relates to drug-eluting coatings, which allow release of the incorporated drug in such a way that the performance of the device can be enhanced/optimized or that undesired events such as infection or inflammation can be prevented or reduced. More particularly, this invention relates to bioresorbable polymer coatings which include a pharmacologically/biologically active agent encapsulated in a polymer matrix comprising multi-block co-polyester such as, for example, urethane linked multi-block co-polyesters consisting of a poly(glycolide-caprolactone) or a poly(glycolide-lactide) segment on the one hand and a poly(D,L- Lactide)-segment on the other hand, the segments having different physical and degradation characteristics as to optimize the handling properties of the device and release characteristics of the incorporated drug.

Preferred examples of bioactive agents with which a copolymer according to the invention may be loaded to provide a pharmaceutical composition for delivery of said agents include amino acids, (poly)peptides, proteins, nucleic acids, polysaccharides, steroids, growth factors, CNS drugs, antibiotica, antigens, chemotherapeutic agents, hormones, antibiotics, antivirals, antifungals, immunosuppressants, antihistamines, anticoagulants, antiphoto-aging agents, melanotropic peptides, anti-inflammatory compounds, antipsychotics, radiation absorbers, decongestants, neuroactive agents, anesthetics, sedatives, vitamins, diagnostics (including radioactive isotopes and fluorescent agents).

Delivery systems may be formulated into microspheres, injectable gels, sheets, rods, cylinders, wafers, etc, by methods known to those skilled in the art, including solvent casting, extrusion, compression moulding, spray drying, spray freeze drying, (multiple) emulsion methods, super critical fluid technology, solvent extraction, phase separation, coacervation, etc. Delivery systems may be formulated into coatings by methods known to those skilled in the art, including dip-coating, dip-moulding, spray-coating, plasma coating, etc.

As will be illustrated in the examples below, the materials of the present invention have improved properties, in particular for drug delivery applications compared to copolymers described in the prior art.

EXAMPLES

General Methods:

The following analytical methods were used in all examples, unless indicated otherwise.

The intrinsic viscosity was measured in chloroform at 25° C. using an Ubbelohde viscometer (according to ISO standard 1628-1).

Monomer conversion, pre-polymer and copolymer composition were determined using $^1$H-NMR at 300 MHz in solutions in deuterated chloroform.

Thermal properties were determined using a TA Instruments-Q1000 MDSC, 1-3 mg dry samples being heated at a rate of 10° C. per minute, cooled down at a rate of 10° C. per minute, hold for 1 minute at −90° C. and heated again at a rate of 10° C. per minute. Glass transition temperature, Tg, is determined from the DSC curve.

The stress strain behavior was determined on an Instron 4301 tensile tester. Thin films (0.25 mm) were measured at room temperature at a cross-head speed of 10 mm/minute. The ultimate tensile strength, the stress at 250% strain, the elongation at break and the initial modulus were determined from these measurements.

Films were prepared by solvent casting a solution of copolymer in chloroform in a petri-dish during 24 hrs at room temperature and subsequently vacuum-drying at 40° C. until constant weight.

Particle size distribution (PSD) of microspheres was measured with a Coulter Counter Multisizer using a 560 μm orifice. About 10 ml microsphere/water suspension was added to about 40 ml of aqueous solution of NaCl in milli-Q water (1% w/w) weak electrolyte solution).

Freeze-dried microspheres were analyzed by cryogenic scanning electron microscopy (cryo-SEM, Jeol, JSM 6301 F) at −120° C. Prior to scanning, the samples were sputtered with a 3 nm palladium-gold layer.

For swelling and in vitro degradation (mass loss) testing, test samples of approximately 1 cm×2 cm×0.25 mm were cut from solvent-cast films and incubated in phosphate buffer solution (PBS, pH 7.4) at 37° C. After pre-determined time intervals, samples were removed from the solution, excess surface water was removed with a tissue, and wet sample weight was determined with an analytical balance. Subsequently, test samples were dried at 40° C. under vacuum until constant weight where after samples were weighed again.

For in vitro release studies, test samples, whether drug loaded microspheres or drug-loaded sheets prepared by cutting pieces (few cm², 50-60 mg material) out of the solvent cast films, were incubated at 37° C. in 3 ml PBS solution (pH 7.4) containing NaN$_3$ (0.02% w/w). Samples were taken after 1 and 3 hours the first day, then every day during the first week and finally once a week. In case of sheets, test samples were carefully removed from the buffer solution and placed in fresh buffer each time a sample was taken. In the case of microspheres, test samples were centrifuged (4000 rpm, 5 min) and the supernatant was collected. Microspheres were then re-suspended in the incubation buffer, as described above. Sample solutions containing leuprolide acetate were analyzed for drug content using RP-HPLC coupled to a UV detector (RP-C18 column, 250×4.6 mm, 5 μm particles, λ 220 nm[leuprolide acetate]=10-200 μg/ml (in PBS), eluents: A) 0.04% phosphoric acid (85%) in water; B) 0.04% phosphoric acid in acetonitrile, gradient A/B 95:5 to 50:50 in 20 min, flow rate 1 ml/min, volume injected 20 μl). Samples containing FITC dextran were analyzed by fluorimetry using a micro plate reader (exc. 493 nm, em 515 nm, [FITC-Dextran]=0.25-10 μg/ml. Samples with progesterone were analysed by UV spectrophotometry (248 nm). The drug loading of the microspheres was indirectly calculated from the amount of drug found back in the PVA solution as well as the different wash solutions. The quantification of the drug that was not encapsulated was performed using the analytical methods described above.

Examples of Synthesis of Pre-polymers

Example 1 poly(glycolide-ε-caprolactone) Pre-polymer (Mn=2000): $(GA_{50}CL_{50})_{2000}$ 70.90 grams (0.611 mol) of glycolide (Purac, The Netherlands) was introduced into a three-necked bottle under nitrogen atmosphere and was dried under vacuum at a pressure of less than 0.01 mbar and at 45° C. for at least 8 hours. ε-Caprolactone (Acros, Belgium) was dried over $CaH_2$ and distilled under reduced pressure in a nitrogen atmosphere. 68.57 grams (0.600 mol) ε-caprolactone was added under a nitrogen flow. 6.55 grams (72.7 mmol) of 1,4-butanediol (Acros, distilled from 4 Å molecular sieves after drying for 8 hours) was added. 68.2 mg stannous octoate (Sigma Corp) was added (M/I=7628:1). The mixture was magnetically stirred and reacted at 130° C. during 168 hours, where after a complete monomer conversion was observed.

An amorphous hydroxyl terminated pre-polymer with a glycolide-ε-caprolactone ratio of 51:49 and with a Tg of −35° C. was obtained

Example 2 poly(glycolide-D,L-Lactide) Pre-polymer (Mn=2000): $(GA_{50}LA_{50})_{2000}$ 90.67 grams (0.638 mol) DL-Lactide (Purac, The Netherlands) and 76.40 grams (0.658 mol) glycolide (Purac, the Netherlands) were introduced into a three-necked bottle under nitrogen atmosphere and were dried under vacuum at a pressure of less than 0.01 mbar and at 45° C. for at least 8 hours. 7.77 grams (86.2 mmol) of 1,4-butanediol (see example 1 for purification) was added. 77.3 mg stannous octoate (Sigma Corp) was added (M/I=7364:1). The mixture was magnetically stirred and reacted at 130° C. during 168 hours where after a complete monomer conversion was observed. An amorphous pre-polymer with a DL-lactide:glycolide ratio of 51:49 and with a Tg of 21° C. was obtained.

Example 3 poly(DL-Lactide) Pre-polymer (Mn=4000): $(LA)_{4000}$ 171.83 grams (1.209 mol) DL-Lactide (Purac, The Netherlands) was introduced into a three-necked bottle under nitrogen atmosphere and was dried under vacuum at a pressure of less than 0.01 mbar and at 45° C. for at least 8 hours. 3.97 grams (44.0 mmol) of 1,4-butanediol (see example 1 for purification) was added. 84.1 mg stannous octoate (Sigma Corp) was added (M/I=6038). The mixture was magnetically stirred and reacted at 130° C. during 168 hours, where after a complete monomer conversion was observed. An amorphous pre-polymer with a Tg of 35° C. was obtained.

Example 4 poly(glycolide-ε-caprolactone) Pre-polymer initiated with PEG600 (Mn=1200): $(GA_{50}CL_{50}PEG600)_{1200}$ 16.57 grams (0.143 mol) glycolide (Purac, The Netherlands) was introduced into a three-necked bottle under nitrogen atmosphere and was dried in vacuum at a pressure of less than 0.01 mbar and at 45° C. for at least 8 hours. ε-Caprolactone (Acros, Belgium) was dried over $CaH_2$ and distilled under reduced pressure in a nitrogen atmosphere. 15.76 grams (0.138 mol) ε-caprolactone was added under a nitrogen flow. The ε-caprolactone and the glycolide were mixed at 60° C. 32.27 grams (53.8 mmol) of PEG600 (Merck, dried in vacuum at 0.008 mbar) for at least 8 hours at 90° C.) was added. After this, the mixture was magnetically stirred at a temperature of 140° C. until the mixture became homogeneous. 14.1 mg stannous octoate (Sigma Corp) was added (M/I=8069:1). The reaction was continued during 168 hours at 140° C., where after a complete monomer conversion was observed. The Tg of the pre-polymer was determined by DSC and was −49° C. A PEG-initiated pre-polymer with a glycolide-ε-caprolactone ratio of 51:49 was obtained.

Examples of Synthesis of Urethane-linked Multi-block Copolymers

Example 5

General Polymerization Method of Urethane Linked Multi-block Copolymers in Bulk

The pre-polymers were pre-heated at 70-130° C. until they became liquid. The appropriate amounts (w/w %) of the pre-polymers were weighed into a glass ampoule supplied with nitrogen inlet and a mechanical stirrer. The contents of the ampoule were heated to 80-110° C. and were mechanically stirred until the pre-polymer mixture became homogeneous. One equivalent of 1,4-butanediisocyanate (Bayer, Germany, distilled at reduced pressure) was added under vigorous stirring. The temperature was then lowered to 80° C. Stirring was stopped when the mixture became too viscous (between 0.5-1.5 hours) where after heating was continued for a period of 24 hours at maximum. The ampoule was cooled to room temperature and the contents were isolated from the ampoule by dissolving the polymer in chloroform. The polymer solution was filtered using a glass-filter, after which the solution was precipitated in ethanol. The polymer was collected, vacuum-dried (40° C.) until constant weight and then stored in a sealed package at 4° C.

Example 6

Urethane Linked $50(GA_{50}CL_{50})_{2000}$-$50(D,L-LA)_{4000}$ Multi-block Copolymers The polymer was prepared according to the method given in example 5. The (GA/CL) pre-polymer of example 1 was pre-heated at 70° C. until it became more liquid; the DLLA pre-polymer of example 3 was pre-heated at 130° C. The pre-polymers were introduced into the glass ampoule in a 50/50 w/w % ratio. The reaction temperature and time were 80° C. and 20 hrs, respectively. The intrinsic viscosity of the polymer was 0.9 dl/g.

Example 7

General Polymerization Method of Urethane Linked Multi-block Copolymers in Solution The pre-polymers were pre-heated at 70-130° C. until they became liquid. The appropriate amounts (w/w %) of the pre-polymers were weighed into a three-necked bottle supplied with nitrogen inlet and a mechanical stirrer. The pre-polymers were heated to 80° C. and were dissolved in freshly distilled 1,4-dioxane (distilled from sodium) to obtain a solution of 50-80 wt. % of pre-polymer. The solution was mechanically stirred until it became homogeneous. One equivalent of 1,4-butanediisocyanate (Bayer, Germany, distilled at reduced pressure) was added under vigorous stirring. When the mixture became viscous (within a few minutes) the solution was diluted with a small amount of solvent. This procedure was repeated every time the solution became viscous. The diluted solution with a concentration of 30-40 wt. % was stirred at 80° C. for a period of 24 hours at maximum. The solution was diluted to 5-10 wt. % and cooled down to ambient temperature. A few drops of i-propanol were added to quench unreacted isocyanate groups. The polymer solution was precipitated in an excess of water. The polymer was collected, washed with water, frozen and subsequently freeze-dried. Finally, the polymer was dried in a vacuum oven until constant weight and then stored in a sealed package at 4° C.

Example 8

Urethane Linked $50(GA_{50}LA_{50})_{2000}$-$50(D,L$-$LA)_{4000}$ Multi-block Copolymers The polymer was prepared according to the method given in example 7. The (GA/LA) pre-polymer of example 2 and the DLLA pre-polymer of example 3 were pre-heated at 130° C. until they became more liquid. The pre-polymers were introduced into the three-necked bottle in a 50/50 w/w % ratio and were diluted with 1,4-dioxane to a 70 wt. % solution. After addition of 1,4-butanediisocyanate, the reaction mixture was diluted with 1,4-dioxane to 35 wt. % in a period of 1 hour. The reaction temperature and time were 80° C. and 24 hrs, respectively. The intrinsic viscosity of the polymer was 1.2 dl/g.

Example 9

Urethane Linked $20(GA_{50}CL_{50}PEG600)_{1200}$-$80(GA_{50}LA_{50})_{2000}$ Multi-block Copolymers The polymer was prepared according to the method given in example 7. The (GACLPEG600) pre-polymer of example 4 was pre-heated at 60° C. until it became more liquid; the (GALA) pre-polymer of example 2 was pre-heated at 130° C. The pre-polymers were introduced into the three-necked bottle in a 20/80 w/w % ratio and were diluted with 1,4-dioxane to a 70 wt. % solution. After addition of 1,4-butanediisocyanate, the reaction mixture was diluted to 40 wt. % in a period of 1 hour. The reaction temperature and -time were 80° C. and 22 hrs, respectively. The intrinsic viscosity of the polymer was 0.75 dl/g.

Examples of Preparation of Drug-loaded Microspheres and Films

Example 10 leuprolide Acetate Loaded $50(GA_{50}CL_{50})_{2000}$-$50(D,L LA)_{4000}$ Microspheres Leuprolide acetate (LeuAc) loaded microspheres were prepared using a water-in-oil-in-water (w/o/w) double emulsion solvent evaporation method. 10 ml of an aqueous solution of 25 mg LeuAc/ml was added to a solution of 1 g $50(GA_{50}CL_{50})_{2000}$-$50(D,L LA)_{4000}$ copolymer in 10 ml of dichloromethane. By vigorous stirring of this mixture with an Ultra Turrax (19,000 rpm for 30 seconds), a stable w/o emulsion was obtained. The stabilised W/O emulsion was added drop-wise at a rate of approximately 5 ml/min to 900 ml of a filtered 3% polyvinyl alcohol (PVA 4-88, Mw=22.000) solution, while stirring the latter at a rate of 400 rpm. After the w/o emulsion had been added, vacuum was applied (800 mbar) for 4 hrs leading to the evaporation of the dichloromethane. The temperature of the PVA solution was kept between 2-5° C. and the stirring rate was kept constant at 400 rpm. The mixture was then poured into a beaker glass to allow the microspheres to settle. Excess solution was removed from the microspheres and the microspheres were washed twice with 800 ml ice-cold demi-water. The microspheres were collected, freeze dried and then stored in the refrigerator. According to this method, solid microspheres with a mean particle size ($d_{50}$) of 50-60 μm were obtained. The encapsulation efficiency was 70% (indirect measurement, see general methods), indicating a loading of 17% (w/w).

Example 11

FITC-Dextran Loaded $25(GA_{50}CL_{50})_{2000}$-$75(D,L$-$LA)_{4000}$ Microspheres According to the method described in Example 10, an aqueous solution of FITC-Dextran (270 mg in 5.5 ml water) was added to a $25(GA_{50}CL_{50})_{2000}$-$75(D,L LA)_{4000}$ copolymer solution (1 g in 17 ml DCM) and vigorously stirred using an Ultra-Turrax (18,000 rpm, 30 sec). The latter w/o emulsion was slowly added to a 5% PVA solution while stirring (400 rpm). After completion of the addition, vacuum was applied (800 mbar) and stirring (400 rpm) was continued for 4 hours to yield microspheres ($d_{50}$ of 50-60 □m). The isolation of the microspheres was performed as described in Example 7. An encapsulation efficiency of 37% and a loading of 10% were obtained.

Example 12

Progesterone Loaded $50(GA_{50}CL_{50})_{2000}$]-$50(D,L$-$LA)_{4000}$ Microspheres Progesterone loaded microspheres were prepared using a o/w simple emulsion solvent evaporation method. An amount of 250 mg progesterone was added to a solution of 1 g $50(GA_{50}CL_{50})_{2000}$-$50(D,L$-$LA)_{4000}$ copolymer in 20 ml of dichloromethane. The resulting solution was added drop-wise at a rate of approximately 5 ml/min to 900 ml of a filtered 3% polyvinyl alcohol (PVA 4-88, Mw=22.000) solution, while stirring at a rate of 400 rpm. When addition was complete, vacuum was applied (800 mbar) for 4 hrs leading to the evaporation of the dichloromethane and the hardening of the microspheres. The temperature of the PVA solution was kept between 2-5° C. and the stirring rate was kept constant at 400 rpm. The isolation of the microspheres was performed as described in Example 7. An encapsulation efficiency of 30% and a loading of 7% were obtained.

Example 13 leuprolide Acetate Loaded $50(GA_{50}CL_{50})_{2000}$-$50(D,L LA)_{4000}$ Films

Films containing 20% (w/w) LeuAc and with an average thickness of 80 μm were prepared by adding a solution of 146.2 mg LeuAc in 740 µl water (200 mg/ml) to a solution of 739.9 mg of 50(GA$_{50}$CL$_{50}$)$_{2000}$-50(D,L-LA)$_{4000}$ in 7.39 ml DCM (10% w/w). After vigorous stirring with an Ultra Turrax (18,000 rpm, 30 sec), the obtained w/o emulsion was solvent casted using a casting knife followed by freeze-drying overnight.

Example 14

FITC-Dextran Loaded 50(GA$_{50}$CL$_{50}$)$_{2000}$-50(D,L LA)$_{4000}$ Films

Films containing 20% (w/w) FITC-Dextran and with an average thickness of 80 µm were prepared by adding a solution of 148.8 mg FITC-Dextran in 741.44 µl water (200 mg/ml) to a solution of 741.4 mg of 50(GA$_{50}$CL$_{50}$)$_{2000}$-50(D,L-LA)$_{4000}$ in 7.4 ml DCM (10% w/w). After vigorous stirring with an Ultra Turrax (18000 rpm, 30 sec) the obtained w/o emulsion was solvent casted using a casting knife followed by freeze-drying overnight Example 15

Progesterone Loaded 50(GA$_{50}$CL$_{50}$)$_{2000}$-50(D,L LA)$_{4000}$ Films

Films containing 24.5% (w/w) progesterone and with an average thickness of 80 µm were prepared by adding 185 mg progesterone to a solution of 750 mg 50(GA$_{50}$CL$_{50}$)$_{2000}$-50(D,L-LA)$_{4000}$ in 7.5 ml of DCM (10% w/w). The homogeneous solution was solvent cast using a casting knife.

Results and Discussion

Summary:

Urethane-linked multi-block co-polyesters containing segments or 'blocks' with different monomer composition and the segments being coupled by an aliphatic diisocyanate chain extender, and the segments being randomly distributed over the polymer chain were prepared. Multi-block copolymers containing 50 wt. % of a poly(glycolide-ε-caprolactone) segment (Mn=2000) and 50 wt. % of a poly(DL-lactide) segment (Mn=4000) or poly(DL-lactide-glycolide) segment (Mn=2000), which were chain extended by 1,4-butanediisocyanate, are flexible, amorphous thermoplastic elastomers. This type of material appears to exhibit excellent characteristics for the preparation of injectable microspheres or as drug eluting medical device coating for the controlled release of drugs.

As a reference material, urethane linked terpolymers of randomly distributed D,L-Lactide, ε-caprolactone and glycolide monomers were prepared by chain-extending one type of pre-polymer. These urethane-linked terpolymers have a similar chain-extender content and overall monomer composition, but a different monomer distribution (which is homogeneous) as the above mentioned multi-block copolymers.

Due to their random monomer distribution, these urethane linked GA/LA/CL terpolymers possess different thermal and mechanical properties as compared to the multi-block copolymers with a controlled monomer distribution over the two blocks. The different polymer properties are caused by a different monomer distribution: in a multi-block co-polyester such as the polylactide and poly(glycolide-ε-caprolactone) based co-polyester of Example 6 (50(GA$_{50}$CL$_{50}$)$_{2000}$-50(D,L-LA)$_{4000}$), the average sequence length of the monomers will be longer and the sequence length distribution will be much smaller than in the urethane linked terpolymer with it's 'random' monomer distribution.

Due to their controlled monomer distribution, the two segments in multi-block copolymers exhibit different physico-chemical, thermal and mechanical properties, which may lead to a certain degree of phase separation. For example, using differential scanning calorimetry (DSC), two very distinct thermal phase transitions (glass transition temperatures) are observed for (GA$_{50}$CL$_{50}$)$_{2000}$-(LA)$_{4000}$ multi-block copolymers. Although not for all segmented multi-block copolymers two distinct thermal transitions can be detected by DSC (e.g. (GA$_{50}$CL$_{50}$)$_{2000}$-(GA$_{50}$LA$_{50}$)$_{2000}$), the segments are still phase separated to a certain extent, as can be concluded from the biphasic degradation (mass loss versus time) characteristics of this polymer. Using DSC, the phase separation can only be observed for multi-block copolymers composed of segments with two very distinct thermal transitions, but the in vitro degradation data provide evidence that multi-block copolymers with only one thermal transition as observed by DSC, still have a (micro) phase separated morphology.

Due to the phase-separated morphology and different monomer composition of the segments of multi-block co-polymer, drugs encapsulated in this type of multi-block copolymers may be distributed in-homogeneously over these two phases, and/or may be released at different rates from these different phases, due to differences in permeability and degradation characteristics of the segments. As a consequence, both biphasic and linear release profiles can easily be obtained by modifying the monomer composition of the segments.

The urethane-linked terpolymers most probably behave very differently in drug delivery applications than the segmented multi-block co-polymers with controlled monomer sequence.

Polymers with a non-phase separated morphology, such as the urethane linked terpolymer, actually exhibit one phase with properties representing the average of that of the different compounds it is composed of, i.e. e.g. only one glass transition temperature instead of two glass transition temperatures as observed for the phase-separated multi-block copolymers, or only one average degradation rate for the whole phase instead of two separate degradation rates for the two distinct phases. Consequently, these polymers do not exhibit phases with different permeability and release rates.

Results:

Effect of Pre-polymer Composition, Content and Length on Properties of Multi-block Co-polymers.

Urethane-linked multi-block co-polyesters with structure (ab)r consisting of two segments with different monomer composition were prepared. For example, a poly(glycolide-ε-caprolactone) segment with or without PEG, in combination with a poly(D,L-lactide) or poly(D,L-lactide-glycolide) segment were prepared. Table 1 shows the composition and the thermal properties of the pre-polymers of which these multi-block copolymers were prepared.

TABLE 1

| Thermal properties of pre-polymers | |
|---|---|
| Pre-polymer | Tg 1$^{st}$ scan (° C.) |
| (LA)4000 | 35 |
| (LA$_{50}$GA$_{50}$)2000 | 21 |
| (GA$_{50}$CL$_{50}$)2000 | −35 |
| (GA$_{50}$CL$_{50}$PEG600)1200 | −49 |
| (GA$_{50}$CL$_{50}$PEG1000)2000 | −49 |
| (GA$_{50}$LA$_{26}$CL$_{24}$)2060 | −8 |
| (GA$_{27}$LA$_{45}$CL$_{28}$)2565 | −6 |

Table 2 gives an overview of the composition, intrinsic viscosity (IV) and thermal properties of the different urethane-linked terpolymers with random monomer distribution, and urethane-linked multi-block copolymers, composed of two segments with different monomer composition. Entries 1-6 represent multi-block copolymers without PEG, whereas entries 9-12 represent multi-block copolymers with PEG in one of the segments. For comparison, urethane-linked terpolymers (entries 7, 8) prepared by chain-extending terpolymers composed of glycolide, lactide and ε-caprolactone with 1,4-butanediisocyanate (BDI) are shown. The so obtained urethane linked terpolymers have a random monomer distribution with a similar GA/CL/LA composition as those of the segmented multi-block co-polymers composed of two different pre-polymers with a controlled monomer distribution. The molecular weight of the random 'terpolymers' was chosen in such a way that the urethane-linked terpolymers had a similar BDI content as the segmented multi-block copolymers to which they are compared.

2. This co-polymer has a Tg of 48° C. The lower $2^{nd}$ Tg of the multi-block co-polymer is caused by partly phase mixing of the two pre-polymer segments. The copolymer with a 50/50 ratio of the two pre-polymers (entry 2) shows also two phase-transitions in the second scan. This clearly demonstrates that there is a certain extent of phase separation of the segments present in the amorphous copolymers containing poly(D,L-lactide) segments.

The polymers from Table 2 with a poly(glycolide-DL-lactide) segment (entries 4, 5 and 6) do not show this thermal behavior. This can be explained by the fact that the monomers are much more randomly distributed over the copolymer: glycolide is present in both segments and these segments may become more compatible with each other.

When the thermal properties of the multi-block co-polymers with two different segments are compared to those of the urethane-linked terpolymers with a similar but randomly distributed monomer composition, the observed Tg's are not the

TABLE 2

Composition, intrinsic viscosity and thermal properties of urethane-linked multi-block co-polyesters and terpolymers

| Nr | Pre-polymer ratio (w/w %) in polymer | Content (w/w %) PEG | Content (w/w %) BDI | Monomer ratio (mol/mol/mol) GA | Monomer ratio (mol/mol/mol) LA | Monomer ratio (mol/mol/mol) CL | IV (dl/g) | Tg 1st scan (°C.) | Tg $2^{nd}$ scan (°C.) |
|---|---|---|---|---|---|---|---|---|---|
| 0 | 100[LA$_{4000}$] | — | 3 | 0 | 1 | 0 | — | 45.7 | 47.7 |
| 1 | 27(GA$_{50}$CL$_{50}$)$_{2000}$-73(LA)$_{4000}$ | — | 4 | 1 | 6 | 1 | 1.32 | 19.9 | 21.4 |
| 2 | 51(GA$_{50}$CL$_{50}$)$_{2000}$-49(LA)$_{4000}$ | — | 5 | 1 | 2 | 1 | 0.91 | −11.9/29.4 | −7/24 |
| 3 | 76(GA$_{50}$CL$_{50}$)$_{2000}$-24(LA)$_{4000}$ | — | 6 | 1 | 0.6 | 1 | 0.84 | −13.3/31.3 | −8.7 |
| 4 | 26(GA$_{50}$CL$_{50}$)$_{2000}$-74(LA$_{50}$GA$_{50}$)$_{2000}$ | — | 7 | 4 | 3 | 1 | 0.45 | 14.6 | 18.3 |
| 5 | 49(GA$_{50}$CL$_{50}$)$_{2000}$-51(LA$_{50}$GA$_{50}$)$_{2000}$ | — | 7 | 2 | 1 | 1 | 0.75 | 2.7 | 5.1 |
| 6 | 75(GA$_{50}$CL$_{50}$)$_{2000}$-25(LA$_{50}$GA$_{50}$)$_{2000}$ | — | 7 | 4 | 1 | 3 | 0.92 | −8.2 | −10.7 |
| 7 | 100(GA$_{50}$LA$_{26}$CL$_{24}$)$_{2060}$ | — | 7 | 50 | 26 | 24 | 0.62 | 6.1 | 11.7 |
| 8 | 100(GA$_{27}$LA$_{45}$CL$_{28}$)$_{2585}$ | — | 5 | 27 | 45 | 28 | 0.67 | 7.1 | 9.5 |
| 9 | 31(GACLPEG600)$_{1200}$-69(LA)$_{4000}$ | 14.8 | 6 | 1 | 10 | 1 | 1.31 | 11.7 | 6.8 |
| 10 | 51(GACLPEG600)$_{1200}$-49(LA)$_{4000}$ | 23.5 | 7 | 1 | 4 | 1 | 1.10 | −21.4 | −23.9 |
| 11 | 27(GACLPEG1000)$_{2000}$-73(LA)$_{4000}$ | 13.5 | 4 | 1 | 9 | 1 | 0.61 | 15.6 | 11.1 |
| 12 | 53(GACLPEG1000)$_{2000}$-47(LA)$_{4000}$ | 26.5 | 5 | 1 | 4 | 1 | 0.91 | −24 | −24 |

Thermal Properties

Urethane-linked multi-block copolymers composed of a diol or PEG-initiated poly(glycolide-ε-caprolactone) segment on the one hand and a poly(D,L-lactide) or poly(D,L-lactide-glycolide) segment on the other hand were completely amorphous (Table 2). No crystalline PEG was present in the pre-polymers (Table 1) and co-polymers with PEG600 as well as PEG1000 initiated pre-polymers.

In general, the glass transition temperature of the urethane-linked multi-block copolymers increases with higher lactide content whereas Tg decreases with increasing ε-caprolactone content. When PEG is used as an initiator, the glass transition temperature is lower than that of the multi-block copolymers composed of only butanediol-initiated pre-polymers.

Most of the urethane-linked multi-block co-polymers of Table 2 exhibit only one glass transition temperature in the first scan. However, (GA$_{50}$CL$_{50}$)$_{2000}$-(D,L-LA)$_{4000}$ multi-block copolymers with a poly(D,L-Lactide) content of 50% and 25% (entries 2 and 3 in Table 2) have two distinct glass transitions, a first Tg around −12° C. and a second one around 30° C.

The latter Tg is the result of the poly(DL-Lactide) rich phase. This glass transition temperature is, however, lower than that of the multi-block co-polymer that is based completely on chain-extended poly(DL-Lactide): entry 1 of Table same. Examples are entries 5 and 7 of Table 2 having a GA:LA:CL ratio of 2:1:1 and entries 2 and 8 with a monomer ratio of 1:2:1.

Whereas the copolymer of entry 2 is phase separated (as shown by it's two Tg's), the chain-extended random terpolymer of entry 8 with the same monomer composition as copolymer 2 has only one Tg. This is an illustration of polymers with a similar composition, having different thermal properties, an effect that can be created by the present multi-block co-polymer technology.

Also, the terpolymer of entry 7 has a higher Tg than that of the multi-block co-polymer with the same composition but with a controlled monomer sequence length (entry 5), which implies that the thermal properties are not only determined by the monomer composition, but also by their distribution over the polymer chain.

The segmented co-polymers comprising two different pre-polymers with controlled monomer sequence lengths may be more suitable for drug delivery applications than the copolymers based on one pre-polymer with a random monomer distribution, due to their (micro)phase separation. Although most of the segmented multi-block co-polymers can be characterized by only one thermal phase transition (which sometimes is very broad and looks like an overlap of more phase transitions), the segments can be more or less phase separated. The phase separation can only be observed clearly for copolymers with a very particular composition by standard thermal analysis techniques such as DSC, but this does not mean that phase separation does not occur in other copolymers were only one thermal transition is observed. By the use of other analytical methods, the phase separation can most probably be observed.

Although two distinctive Tg's are observed for multi-block copolymers comprising poly (lactide) segments with Mn=4000 (entries 2 and 3 of Table 2), this behavior is not observed for similar copolymers with smaller poly (lactide) segments, for example segments with Mn=2000. Multi-block co-polymers with a poly(D,L-Lactide) pre-polymer with a molecular weight of 5000-7000 show an even better phase separation, since the phase transitions become more clear with increasing length of the poly (lactide) segment. The maximum Tg is found around 35° C., which is a few degrees higher than that of a copolymer containing poly (D,L-Lactide) segments with Mn=4000. This indicates that the thermal properties (and therefore also other properties) can be tuned by varying the pre-polymer molecular weights. Furthermore, changing the segment length alters the content of initiator and chain-extender, which also affects the thermal properties. Thus, by changing the length of the pre-polymers, the properties of the copolymer can be changed while keeping the same monomer composition. This is not possible with the multi-block co-polymers from the prior art.

This method is only applicable to the multi-block co-polymers with a random distribution of segments (structure (ab)r). In multi-block co-polymers with alternating pre-polymer segments (e.g with structure (ab)n), the monomer composition will change when the length of the segments is changed. Depending on the type of application, the desired properties such as degradation time, swelling behavior or release properties can be obtained by choosing the right combination of pre-polymer composition, pre-polymer length and ratio of pre-polymers in the final multi-block copolymer. Therefore, the multi-block co-polymers with randomly distributed segments are highly preferred.

multi-block-copolymers with random and controlled monomer distribution are similar. Table 3 shows the mechanical testing results.

FIG. 1a shows the stress-strain behavior of co-polymers with entry nr 2 and 8 of Table 2. It is clearly shown that the mechanical behavior of these polymers is significantly different. The multi-block co-polymer consisting of two different segments, i.e. 50% (w/w) of poly(lactide) segments with Mn of 4000 and 50% (w/w) of poly (glycolide-caprolactone) segments with Mn of 2000 (entry nr. 2) has a phase separated structure, which is demonstrated by the presence of two separate glass transition temperatures: $Tg1=-11.9°$ C., $Tg2=+29.4°$ C. Since the first phase transition temperature is below room temperature and the second thermal transition is found at a temperature above mechanical testing temperature (which is room temperature) this co-polymer behaves as an elastomer. Due to the phase separation which results in a morphology with 'hard' and 'soft' domains, an elastomeric multi-block co-polymer is obtained with a higher modulus and tensile strength as compared to that of the urethane-linked terpolymer consisting of only one segment with a random monomer distribution ($100(GA_{50}LA_{25}CL_{25})_{2565}$).

FIG. 1b shows the stress-strain behavior of co-polymers with entries nr. 5 and 7 of Table 2. It is clearly shown that the mechanical behavior of both polymers is similar.

The multi-block co-polymer of FIG. 1b with entry nr 5 comprising two different pre-polymer segments (GA/CL and GA/LA) and having only one Tg below room temperature has a stress-strain-behavior comparable to that of the completely random urethane-linked terpolymer (entry nr 7). Obviously, the difference in monomer distribution of the two polymers of FIG. 1b is not large enough to result in different mechanical properties. Mechanical properties of the segmented copolymers are therefore dependent on the difference in individual properties of both segments and are a good tool to predict phase separation. However, these results do not imply that a thermally observable phase transition is a prerequisite to obtain such a difference in mechanical properties.

TABLE 3

Mechanical properties of multi-block copolymers with controlled monomer distribution and of urethane-linked terpolymers.

| Polymer | GA/LA/CL ratio (—) | Tg $1^{st}$ scan (° C.) | Tg $2^{nd}$ scan (° C.) | Modulus (MPa) | Stress @ max load (MPa) | Stress @ yield (MPa) | Strain @ break (%) | Stress @ break (MPa) |
|---|---|---|---|---|---|---|---|---|
| Multi-block copolymers with controlled monomer distribution | | | | | | | | |
| $50(DLLA)_{4000}$-$50(GA/CL)_{2000}$ | 1:2:1 | −12/29 | −7/24 | 4.6 | 1.8 | 0.7 | 1455 | 1.8 |
| $50(GA/LA)_{2000}$-$50(GA/CL)_{2000}$ | 2:1:1 | 2.7 | 5.1 | 0.6 | — | 0.3 | — | — |
| Terpolymers with random monomer distribution | | | | | | | | |
| 100(GA/LA/CL) 2565 | 1:2:1 | 7.1 | 9.5 | 1.0 | — | 0.4 | — | — |
| 100(GA/LA/CL) 2060 | 2:1:1 | 6.1 | 11.7 | 1.6 | — | 0.4 | — | — |

Mechanical Properties

In FIGS. 1a and 1b the stress-strain behavior of urethane-linked multi-block co-polymers with controlled monomer distribution are compared with the stress strain behavior of urethane-linked terpolymers with a random monomer distribution. Both the chain-extender (BDI) content and overall monomer contents (percentages GA, LA and CL) of the In vitro Degradation Behavior of Multi-block Copolymers Multi-block Copolymers without PEG Moieties FIG. 2 shows the degradation behavior, as expressed by mass loss of the test samples, of the multi-block copolymers. The figure clearly shows how both segments contribute to the overall mass loss behavior of the multi-block copolymers.

Up to 4 weeks $50(GA/CL)_{2000}$-$50(LA)_{4000}$ and $50(GA/CL)_{2000}$-$50(LA/GA)_{2000}$ exhibit similar degradation behavior, characterized by a mass loss of only 1-2 w/w %. Whereas mass loss of the MBCP with the rigid $(LA)_{4000}$ segment continued with the same trend up to 8 weeks, the MBCP with the more flexible $(LA/GA)_{2000}$ hard segment (with a significantly lower Tg than the $(LA)_{4000}$ segment) showed a rapid mass loss of 60% between 5-8 weeks. After this rapid mass loss a plateau value of 40% remaining mass was observed up to 14 weeks. Around 14 weeks mass loss continued. From 14 weeks onwards the mass loss profile of the MBCP with the $(GA/LA)_{2000}$ segment was comparable to that of the MBCP with the $(LA)_{4000}$ segment.

Contrary to this biphasic mass loss behavior of $50(GA/CL)_{2000}$-$50(LA/GA)_{2000}$, mass loss of the $50(GA/CL)_{2000}$-$50(LA)_{4000}$ multi-block copolymer showed a smooth and gradual pattern. From this it can be concluded that the degradation rates of the LA and the GA/CL segments are similar order of magnitude. The higher degradation rate of glycolide units, as compared to lactide, is probably counterbalanced by the lower degradation rate of caprolactone units as compared to lactide.

Since both multi-block copolymers have one identical segment, i.e. $(GA/CL)_{2000}$, the difference in degradation-induced mass loss behavior is caused by the different chemical composition of the $2^{nd}$ segment. Therefore, the rapid mass loss observed between 5 and 8 weeks for $50(GA/CL)_{2000}$-$50(LA/GA)_{2000}$ obviously originates from preferential degradation of the $(GA/LA)_{2000}$ segment. Due to the incorporation of the more hydrolysable glycolide units, the $(GA/LA)_{2000}$ segments in $50(GA/CL)_{2000}$-$50(LA/GA)_{2000}$ degrade faster than the $LA_{4000}$ segments in $50(GA/CL)_{2000}$-$50(LA)_{4000}$.

Once the $(GA/LA)_{2000}$ segments are degraded so far that no more soluble fragments are formed, further mass loss of the $50(GA/CL)_{2000}$-$50(LA/GA)_{2000}$ multi-block copolymers is temporarily inhibited as the degradation rate of the $(GA/CL)_{2000}$ segment is lower than that of the (GA/LA)2000 segment and degradation has not yet resulted in the formation of soluble degradation products originating from the $(GA/CL)_{2000}$ segment. Only around 14 weeks, degradation of the $GA/CL_{2000}$ segments has continued sufficiently as to form soluble degradation products, resulting in further mass loss. The biphasic degradation pattern of $50(GA/CL)_{2000}$-$50(LA/GA)_{2000}$ provides evidence for micro domain phase separation. Obviously, the $(GA/LA)_{2000}$ segments degrade at a higher rate than the $(GA/CL)_{2000}$ segments.

Multi-block Copolymers with PEG

Due to their hydrophobic character, urethane-linked multi-block copolymers based on segments composed of lactide, glycolide and/or caprolactone absorb only small amounts of water. They can be characterized as non-swellable polymers. However, by introducing more hydrophilic moieties, swellable polymers can be obtained. Multi-block copolymers with a hydrophilic, water swellable segment in combination with a more hydrophobic non-swellable segment can be obtained by introducing PEG into one of the pre-polymers. By varying the composition and content of both segments, both the swelling degree and degradation rate of these multi-block copolymers can be controlled, and consequently the release characteristics can be modified.

Urethane-linked multi-block copolymers composed of a PEG-initiated glycolide-caprolactone segment and a lactide segment (i.e.$30(GA_{50}CL_{50}PEG600)_{1200}$-$70(LA)_{4000}$ and $50(GA_{50}CL_{50}PEG600)_{1200}$-$50(LA)_{4000}$, entries 9 and 10 of Table 2, have highly interesting degradation characteristics. Due to the hydrophilic PEG-containing segments, the multi-block copolymers, which contain 15% and 25% PEG respectively, absorb significant amounts of water (FIG. 3). The higher the PEG content, the faster the water uptake rate. FIG. 2 further shows that the "equilibrium" water content in the period 2-6 weeks is inversely proportional with initial PEG content of the multi-block copolymer. The copolymer with 15% PEG had an "equilibrium" water content of approximately 45-50%, whereas the copolymer with 25% PEG had an "equilibrium" water content of approximately 35%.

Concurrently with the absorption of large amounts of water, the PEG-containing $30(GA/PEG_{600}/CL)_{1200}$-$70(LA)_{4000}$ multi-block copolymer degrades (FIG. 3). Degradation was characterized by a biphasic mass loss profile. Initially, from 0-10 weeks, mass loss was slow but linear due to rapid degradation of the (GA/PEG600/CL) segments and liberation of PEG600 rich fragments from the polymer (mass loss at 8 weeks: 16.5%; overall PEG content: 15 w/w%). After 10 weeks the rate of mass loss increased and the mass loss profile was very similar to that of $50(GA/CL)_{2000}$-$50(LA)_{4000}$ with the same $(LA)_{4000}$ segment.

FIG. 3 clearly shows that the multi-block copolymer with 25% PEG degrades significantly faster than the copolymer with 15% PEG, but again a biphasic mass loss profile is observed.

A significantly higher degradation rate, expressed by mass loss vs. time is obtained when PEG600 is replaced by PEG1000, but keeping the overall weight percentage of PEG constant (these results are not shown). The multi-block copolymers with 25 w/w% PEG1000 very rapidly absorb large amounts of water, but in a few hours the copolymers start to disintegrate/fragment. This is caused by the high water absorption rate and by a higher solubility of low molecular weight PEG1000 containing segments as compared to those of PEG600 containing fragments. By varying the PEG content and the molecular weight of the PEG moieties, the mass loss profile of segmented urethane linked $(GA_{50}CL_{50}PEG)$-$(LA_{4000})$ polymers can be tuned.

Characteristics of Prepared Microspheres

Both the w/o/w/double emulsion solvent evaporation method used for the preparation of leuprolide acetate and FITC-dextran loaded microspheres as well as the simple o/w emulsion solvent evaporation method used to prepare progesterone loaded microspheres yielded spherical microspheres with low surface porosity as was observed from scanning electron microscopy photographs. Mean particle size of the microspheres ranged from 40 to 100 micrometer, as was observed by Coulter counter particle size measurements.

Moreover, it was observed that $50(GACL)_{2000}]$-$50(LA_{4000})$ microspheres were not sticky and could easily be re-suspended, which is considered an important advantage as compared to microspheres composed of lactide-caprolactone (50/50 ratio) which tend to stick together after drying, making it difficult to collect the microspheres as a loose powder.

In vitro release characteristics of $(GA50CL_{50})_{2000}$-$LA_{4000}$ and $(GA_{50}CL_{50})_{2000}$-$(LA_{50}GA50)_{2000}$ multi-block co-polyesters Release from the widely applied poly(glycolide-lactide) and poly(DL-lactide-ϵ-caprolactone) copolymers (PLACL) generally occurs according to a square root of time profile, i.e. a linear release curve is obtained when the cumulative release is plotted verses the square root of time ($t^{0.5}$).

For PGLA-copolymer, this square root of time behavior is caused by the fact that the release of the drug from the microspheres is governed by diffusion of the dissolved drug through pores in the microsphere. Because of the relatively high Tg of PGLA, the PGLA matrix is rigid and impermeable to drug molecules. Consequently, release can only occur through diffusion through the pores. For PLACL, this square root of time behavior is caused by diffusion of the dissolved drug through the relatively permeable, but slowly degrading polymer matrix.

In case of (micro)phase-separated urethane-linked multi-block copolymers containing two different segments, the drug is encapsulated in both of the amorphous phases. Because of the different characteristics of both phases with respect to permeability, swellability and degradation rate, the release rates of the encapsulated drug from these two phases will be different. One phase for example may release the drug at a significantly higher rate than the other phase because of faster degradation or higher swellability. A higher degradation rate of one of the phases may be used to compensate for the increasing diffusion distance of the encapsulated drug and of degradation products. The composition of both segments can be chosen in such a way that the desired overall release profile can be obtained. This is a major advantage over the amorhous random copolymers and homopolymers of the prior art with only one thermal phase.

Release of Model Drugs from Multi-block Copolymers

Release characteristics of the multi-block co-polymers were studied by use of drug-loaded films as these have similar release characteristics as microspheres, but are easier to handle and analyze. Thickness of the films (~80 μm) was comparable to the diameter of the prepared microspheres.

FIG. 4 shows that, except for the burst release, release of encapsulated progesterone from $50(GACL)_{2000}$-$50(LA)_{4000}$ films with 24.5% drug load was linear up to 10 weeks, whereas, release from a lactide-caprolactone copolymer (50/50, IV=1 dl/g) with random monomer composition obeys square root of time kinetics.

Leuprolide acetate release from $50(GA\text{-}CAP)_{2000}$-$50(LA)_{4000}$ films (FIG. 5) was also characterized by a nearly linear release profile in combination with a very small burst release. The release rate appeared to increase slightly with time.

The linear release profiles are caused by a combination of diffusion and ongoing degradation of the polymer matrix. Up to 4-5 weeks release is governed by diffusion of drug molecules through the polymer matrix. Thereafter, ongoing degradation of the polymer results in a more permeable polymer matrix due to which the release rate increases. So, the increase of matrix permeability compensates for the increased diffusion distance, which normally would lead to decreasing release rates with time.

FIG. 6 shows the release characteristics of the polysaccharide FITC-Dextran (MW=4000) from $50(GACL)_{2000}$-$50(LA)_{4000}$ and $50(GACL)_{2000}$-$50(GALA)_{2000}$. Release was characterized by a significant burst, where after for both polymers a period with a very low release rate was observed. For $50(GACL)_{2000}$-$50(GALA)_{2000}$, the release rate then increased gradually and within 50 days FITC dextran release was complete. The burst release of FITC-dextran from $50(GACL)_{2000}$-$50(LA)_{4000}$ was smaller and the release rate of FITC dextran after the burst release, up to 25 days, was initially lower as compared to $50(GACL)_{2000}$-$50(LA)_{4000}$. Between 4 and 5 weeks, a second burst was observed, where after the release rate decreased again. Between 7 and 9 weeks again an increase in the release rate is observed.

The initial burst release for both series represents merely drug present at or near the film surface. Differences in initial burst release are predominantly caused by the preparation method and not by the polymer characteristics and are therefore ignored further. The initially low release rates following the burst release are caused by the relatively high molecular weight of FITC-dextran, due to which FITC-dextran is (partly) entrapped in the multi-block copolymers. Upon degradation of the multi-block copolymers the molecular weight decreases and consequently the polymer free volume and permeability of the polymer matrix increases, resulting in an increased release rate of the drug.

The difference in release patterns of FITC dextran from these two polymers can be explained by taking into account the degree of phase separation of these multi-block copolymers. The $50(GACL)_{2000}$-$50(LA)_{4000}$ multi-block copolymer is phase separated to a high extent as was already concluded from the presence of two distinct glass transition temperatures. The extent of phase separation of the $50(GACL)_{2000}$-$50(GALA)_{2000}$ multi-block copolymer is lower.

The $50(GACL)_{2000}$-$50(LA)_{4000}$ multi-block copolymer is a more rigid polymer as compared to the $50(GACL)_{2000}$-$50(GALA)_{2000}$ multi-block copolymer (see the mechanical testing data). This is expressed by the lower FITC dextran release rate after the initial burst for the $50(GACL)_{2000}$-$50(LA)_{4000}$ multi-block copolymer. Based upon the gradual increase of the FITC dextran release rate from $50(GACL)_{2000}$-$50(GALA)_{2000}$, it seems that the polymer matrix as a whole degrades relatively homogeneously, although this is not in line with the mass loss degradation characteristics shown in FIG. 2. However, it should be taken into account that release precedes mass loss.

In contrast, degradation of $50(GACL)_{2000}$-$50(LA)_{4000}$ is less homogeneous. Based on the biphasic FITC dextran release profile observed for $50(GACL)_{2000}$-$50(LA)_{4000}$, it can be concluded that the two phases, i.e. the $(GA\text{-}CL)_{2000}$ and the $LA_{4000}$ degrade at different rates. It is hypothesized that the burst in the FITC dextran release from $50(GACL)_{2000}$-$50(LA)_{4000}$ multi-block copolymer between 30 and 35 days represents FITC dextran released from the more permeable (lower Tg!) and/or faster degrading $(GA\text{-}CL)_{2000}$ segments of this phase-separated polymer. Release thereafter originates from FITC dextran entrapped in the $LA_{4000}$ phases. Due to its more rigid character and/or slower degradation rate, release from $LA_{4000}$ phases is delayed (drug molecules are initially entrapped) and slower (higher Tg) as compared to release from the more permeable (lower Tg) and faster degrading $(GA\text{-}CL)_{2000}$ phase. Assuming that the drug is homogeneously distributed over the two phases, it appears that around 35 days, all the drug which was initially present in the $(GA\text{-}CL)_{2000}$ phase (appr. 50% of the total drug load) has been released.

The invention claimed is:

1. A biodegradable multi-block copolymer, comprising randomly and non-alternatingly arranged hydrolysable segments each composed of pre-polymer A or pre-polymer B, which segments are randomly and non-alternatingly connected to each other by multi-functional chain extenders,
   wherein the multi-block copolymer is completely amorphous at human body conditions, and
   wherein the multi-block copolymer is loaded with a bioactive agent.

2. A copolymer of claim 1, which has a glass transition temperature below body temperature at human body conditions.

3. A copolymer of claim 1, wherein pre-polymer A and/or pre-polymer-B contain ester and/or carbonate and/or anhydride linkages, optionally in combination with polyethers.

4. A copolymer of claim 1, wherein pre-polymer A comprises polyether groups.

5. A copolymer of claim 1, wherein a polyether is present as an additional pre-polymer.

6. A copolymer of claim 1, wherein pre-polymer A comprises a reaction product of an ester forming monomer selected from the group consisting of diols, dicarboxylic acids and hydroxycarboxylic acids.

7. A copolymer of claim 1, wherein pre-polymer A comprises reaction products of at least one cyclic monomer with at least one non-cyclic initiator selected from the group consisting of diols, dicarboxylic acids and hydroxycarboxylic acids.

8. A copolymer of claim 7, wherein said cyclic monomer is selected from the group consisting of glycolide, lactide (L, D or DL), $\epsilon$-caprolactone, $\delta$-valerolactone, trimethylene carbonate, tetramethylene carbonate, 1,4-dioxane-2-one (para-dioxanone), 1,5-dioxepane-2-one and cyclic anhydrides.

9. A copolymer of claim 8 wherein pre-polymer A contains at least two different cyclic monomers.

10. A copolymer of claim 9 wherein pre-polymer A consists of glycolide and $\epsilon$-caprolactone in a 1:1 weight ratio.

11. A copolymer of claim 9 wherein pre-polymer A consists of glycolide and lactide in a 1:1 weight ratio.

12. A copolymer of claim 7, wherein said non-cyclic initiator is selected from the group of succinic acid, glutaric acid, adipic acid, sebacic acid, lactic acid, glycolic acid, hydroxybutyric acid, ethylene glycol, diethylene glycol, 1,4-butanediol and 1,6-hexanediol.

13. A copolymer of claim 4, wherein said polyether groups are selected from the group consisting of PEG (polyethylene glycol), PEG-PPG (polypropylene glycol), PTMG (polytetramethylene ether glycol) and combinations thereof.

14. A copolymer of claim 13, wherein the polyether group is PEG.

15. A copolymer of claim 14, wherein PEG is an initiator for ring-opening polymerization with a molecular weight between 150-4000.

16. A copolymer of claim 1, wherein pre-polymer A has a number average molecular weight (Mn) between 300 and 30000.

17. A copolymer of claim 1, wherein pre-polymer B comprises $\epsilon$-caprolactone, $\delta$-valerolactone, trimethylene carbonate, para-dioxanone, DL-lactide and/or glycolide.

18. A copolymer of claim 17, wherein pre-polymer B contains d,l-lactide.

19. A copolymer of claim 17, wherein pre-polymer B has a number average molecular weight (Mn) higher than 300.

20. A copolymer of claim 16, wherein pre-polymer B is present in an amount of 10-90 wt. %.

21. A copolymer of claim 1, having an intrinsic viscosity of at least 0.1 dl/g, and less than 6 dl/g.

22. A copolymer of claim 1, wherein the chain extender is derived from a difunctional aliphatic compound.

23. A copolymer of claim 22, wherein the chain-extender is a diisocyanate.

24. The copolymer of claim 1 wherein the bioactive agent is selected from the group consisting of amino acids, (poly) peptides, proteins, nucleic acids, polysaccharides, steroids, growth factors, antigens, chemotherapeutic agents, hormones, antibiotics, antivirals, antifungals, immunosuppressants, antihistamines, anticoagulants, antiphoto-aging agents, melanotropic peptides, anti-inflammatory compounds, antipsychotics, radiation absorbers, decongestants, neuroactive agents, anesthetics, sedatives and vitamins.

* * * * *